United States Patent
Tate et al.

(10) Patent No.: US 12,304,909 B2
(45) Date of Patent: *May 20, 2025

(54) COMPOUNDS AND THEIR USE IN THERAPY

(71) Applicant: IMPERIAL COLLEGE INNOVATIONS LIMITED, London (GB)

(72) Inventors: Edward William Tate, London (GB); Andrew Simon Bell, London (GB)

(73) Assignee: IMPERIAL COLLEGE INNOVATIONS LIMITED, London (GB)

(*) Notice: Subject to any disclaimer, the term of this patent is extended or adjusted under 35 U.S.C. 154(b) by 793 days.

This patent is subject to a terminal disclaimer.

(21) Appl. No.: 17/414,712

(22) PCT Filed: Dec. 19, 2019

(86) PCT No.: PCT/GB2019/053613
§ 371 (c)(1),
(2) Date: Jun. 16, 2021

(87) PCT Pub. No.: WO2020/128473
PCT Pub. Date: Jun. 25, 2020

(65) Prior Publication Data
US 2022/0064158 A1   Mar. 3, 2022

(30) Foreign Application Priority Data
Dec. 19, 2018 (GB) .................................. 1820659

(51) Int. Cl.
C07D 471/04 (2006.01)
A61K 31/437 (2006.01)
A61K 45/06 (2006.01)
A61P 35/00 (2006.01)

(52) U.S. Cl.
CPC .......... *C07D 471/04* (2013.01); *A61K 31/437* (2013.01); *A61K 45/06* (2013.01); *A61P 35/00* (2018.01)

(58) Field of Classification Search
CPC .. C07D 471/04; C07D 487/04; A61K 31/437; A61K 45/06; A61P 35/00
USPC ....................................................... 514/300
See application file for complete search history.

(56) References Cited

U.S. PATENT DOCUMENTS 10,759,804 B2   9/2020   Bell et al.
2020/0339586 A1   10/2020   Bell et al.

FOREIGN PATENT DOCUMENTS

| WO | WO 00/37464 A2 | 6/2000 | |
| WO | WO 2010/026365 A1 | 3/2010 | |
| WO | WO 2013/083991 A1 | 6/2013 | |
| WO | WO 2017/011907 A1 | 1/2017 | |
| WO | WO-2017001812 A1 * | 1/2017 | ................ A61P 3/10 |
| WO | WO 2020/128475 A1 | 6/2020 | |
| WO | WO 2020/129475 A1 | 6/2020 | |

OTHER PUBLICATIONS

Rodriguez-Hernandez et al., Published Sep. 5, 2023, Nature Communications, vol. 14, Article No. 5408, pp. 1-13 (Year: 2023).*
Bell et al., "Selective Inhibitors of Protozoan Protein N-myristoyltransferases as Starting Points for Tropical Disease Medicinal Chemistry Programs", PLoS Neglected Tropical Diseases, vol. 6, Issue 4, e1625, Apr. 2012, pp. 1-9.
Bryant et al., "Myristoylation-dependent replication and assembly of human immunodeficiency virus 1", Proc. Natl. Acad. Sci. USA, vol. 87, Jan. 1990, pp. 523-527.
Davis et al., "Recombinant VP4 of Human Rhinovirus Induces Permeability in Model Membranes", Journal of Virology, vol. 82, No. 8, Apr. 2008, pp. 4169-4174.
Farazi et al., "The Biology and Enzymology of Protein N-Myristoylation", The Journal of Biological Chemistry, vol. 276, No. 43, Oct. 26, 2001, pp. 39501-39504.
Göttlinger et al., "Role of capsid precursor processing and myristoylation in morphogenesis and infectivity of human immunodeficiency virus type 1", Proc. Natl. Acad. Sci. USA, vol. 86, Aug. 1989, pp. 5781-5785.
International Search Report (PCT/ISA/210) issued in PCT/GB2019/053613, mailed on Feb. 18, 2020.
Lueg et al., "N-myristoyltransferase inhibition is synthetic lethal in MYC-deregulated cancers", bioRxiv, Mar. 20, 2021, pp. 1-25.
Mousnier et al., "Fragment-derived inhibitors of human N-myristoyltransferase block capsid assembly and replication of the common cold virus", Nature Chemistry, vol. 10, No. 6, May 14, 2018, 18 pages.

(Continued)

*Primary Examiner* — Bahar Craigo
*Assistant Examiner* — Jaret J Crews
(74) *Attorney, Agent, or Firm* — Birch, Stewart, Kolasch & Birch, LLP

(57) ABSTRACT

The invention provides inter aliaa compound as defined herein and its use in the prevention or treatment of a disease or disorder in which inhibition of N-myristoyl transferase provides a therapeutic or prophylactic effect, e.g. cancer.

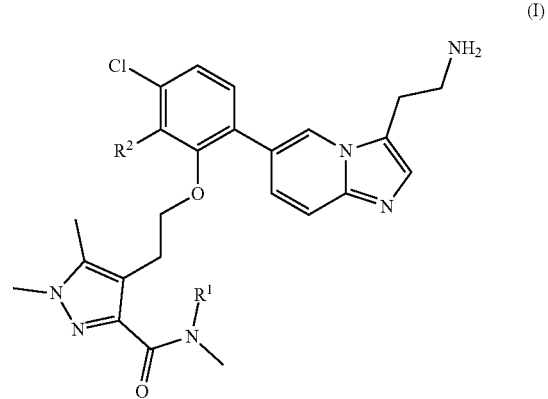

(I)

10 Claims, 1 Drawing Sheet

(56) References Cited

OTHER PUBLICATIONS

Ramljak et al., "Cellular N-myristoyltransferases play a crucial picornavirus genus-specific role in viral assembly, virion maturation, and infectivity", PLoS Pathogens, vol. 14, No. 8, Aug. 6, 2018, pp. 1-39.
Resh, Marilyn D., "Interaction of tyrosine kinase oncoproteins with cellular membranes", Biochimica et Biophysica Acta, vol. 1155, 1993, pp. 307-322.
Written Opinion (PCT/ISA/237) issued in PCT/GB2019/053613, mailed on Feb. 18, 2020.

* cited by examiner

COMPOUNDS AND THEIR USE IN THERAPY

FIELD OF INVENTION

This invention relates to compounds of formula (I), or a pharmaceutically acceptable carbamate or salt thereof, including salts of such carbamates, which have activity as inhibitors of the human N-myristoyl transferases. The invention also relates to uses of such compounds as medicaments, in particular, in the treatment of a disease or disorder in which inhibition of human N-myristoyl transferases provides a therapeutic or prophylactic effect. Such diseases include viral infections (such as human rhinovirus, human immunodeficiency virus (HIV), poliovirus, foot and mouth disease, and enterovirus 71 infections), and hyperproliferative disorders (such as cancers including B-cell lymphoma and leukaemia).

BACKGROUND TO THE INVENTION

N-myristoyl transferase (NMT) is a monomeric enzyme, which is ubiquitous in eukaryotes. NMT catalyses an irreversible co-translational transfer of myristic acid (a saturated 14-carbon fatty acid) from myristoyl-Coenzyme A (myr-CoA) to a protein substrate containing an N-terminal glycine with formation of an amide bond (Farazi, T. A., G. Waksman, and J. I. Gordon, *J. Biol. Chem.*, 2001. 276 (43): p. 39501-39504).

There are two types of human NMT, human NMT1 (HsNMT1) and human NMT2 (HsNMT2). Inhibition of human NMT has been suggested as a target for treating or preventing various diseases or disorders, for example hyperproliferative disorders (for example cancers, e.g. human colorectal cancer, gallbladder carcinoma, brain tumors, and lymphomas such as B-cell lymphoma) (Resh M D. 1993. Biochem. Biophys. Acta 1115, 307-22; Bertiaume L G, Beuachamp E, WO2017011907), and viral infections such as HIV (Gottlinger H G, Sodroski J G, Haseltine W A. 1989. Proc. Nat. Acad. Sci. USA 86:5781-85; Bryant M L, Ratner L. 1990. Proc. Natl. Acad. Sci. USA 87:523-27) and human rhinovirus (HRV) (Davis M P, Bottley, G, Beales L P, Killington, R A, Rowlands D J, Tuthill, T J, 2008 Journal of Virology 82 4169-4174; Mousnier A, Bell A S, Swieboda D P, Morales-Sanfrutos J, Perez-Dorado I, Brannigan J A, Newman J, Ritzefeld M, Hutton, J A, Guedan A, Asfor A S, Robinson, S W, Hopkins-Navratilova I, Wilkinson A J, Johnston S L, Leatherbarrow R J, Tuthill T J, Solari R, Tate E W 2018 Nature Chemistry 10 (6) 599-606), Corbic Ramljak I, Stanger J, Real-Hohn A. Dreier D, Wimmer L., Redlberger-Fritz M, Fischl W, Klingel K, Mihovilovic M D, Blaas D, Kowalski H, PLOS Pathogens 14 (8): e1007203. As NMT plays a key role in protein trafficking, mediation of protein-protein interactions, stabilization of protein structures and signal transduction in living systems, inhibition of the NMT enzyme has the potential to disrupt multi-protein pathways. This is an attractive characteristic to reduce the risk of the development of resistance in, for example, treatment or prevention of microbial infections and hyperproliferative disorders.

There are two binding pockets in NMT. One is the myr-CoA binding pocket and the other is the peptide binding pocket. Most NMT inhibitors reported to date target the peptide binding pocket.

Compounds active as inhibitors of NMT have previously been disclosed, see for example WO00/37464 (Roche), WO2010/026365 (University of Dundee), WO2013/083991 (Imperial Innovations Limited) and WO2017/001812 (Imperial Innovations Limited).

However, there remains a need for further compounds active as inhibitors of N-myristoyl transferase, and in particular those that combine very potent inhibition of human N-myristoyl transferases with an appropriate pharmacokinetic profile for oral administration, for example a long half-life and good oral bioavailability.

Surprisingly, the present inventors have now found that a certain subset of chlorophenyl-substituted imidazo[1,2-a]pyridine compounds having a very specific substitution pattern are highly potent inhibitors of human N-myristoyl-transferases (they have both high enzyme and cell potency), and combine that high potency with good metabolic stability, and in particular a long in vivo half-life. The compounds are also orally bioavailable, and have been shown to prevent tumour growth in mice when orally administered. This combination of properties makes or is expected to make the compounds of the invention especially suitable for use as medicaments and, in particular, medicaments for oral administration, for the treatment of diseases such as cancers.

SUMMARY OF THE INVENTION

The invention provides a compound of formula (I), a pharmaceutically acceptable amide, carbamate or salt thereof, including salts of such amides or carbamates,

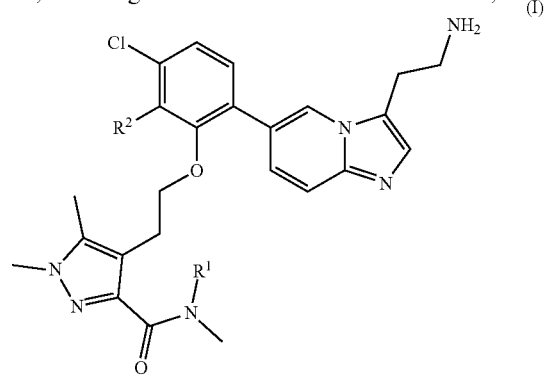

wherein $R^1$ is H or —$CH_3$; and
$R^2$ is H or F (hereinafter referred to as "compounds of the invention").

More particularly, the present invention provides a compounds of formula (Ia) or (Ib), or a pharmaceutically acceptable amide, carbamate or salt of a compound of formula (Ia) or (Ib), including salts of such amides or carbamates:

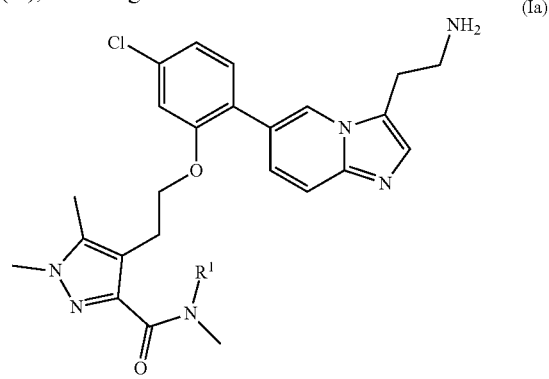

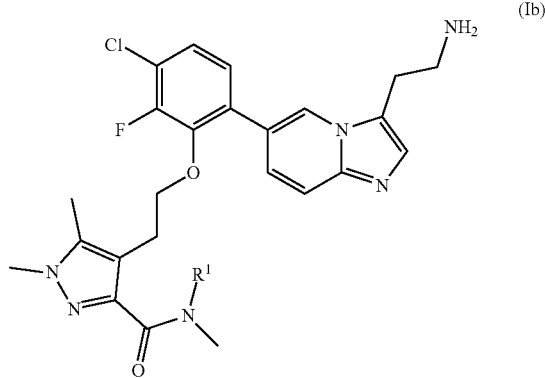

wherein $R^1$ is H or $CH_3$.

Preferably the compound of the invention is a compound of formula (Ia), or a pharmaceutically acceptable amide, carbamate or salt thereof, including salts of such amides or carbamates, particularly, a compound of formula (Ia), or a pharmaceutically acceptable carbamate or salt thereof, including salts of such carbamates, especially, a compound of formula (Ia), or a pharmaceutically acceptable salt thereof.

The invention further provides a pharmaceutical composition comprising a compound according to the invention and a pharmaceutically acceptable carrier.

The invention also provides a compound according to the invention, or a pharmaceutical composition according to the invention, for use as a medicament.

The invention also provides a compound according to the invention, or a pharmaceutical composition according to the invention, for use in the prevention or treatment of a disease or disorder in which inhibition of human N-myristoyl transferases provides a therapeutic or prophylactic effect. The invention also provides use of a compound according to the invention for the manufacture of a medicament for the prevention or treatment of a disease or disorder in which inhibition of human N-myristoyl transferases provides a therapeutic or prophylactic effect. The invention also provides a method of treating or preventing a disease or disorder in which inhibition of human N-myristoyl transferase provides a therapeutic or prophylactic effect in a subject, comprising administering a therapeutically effective amount of a compound according to the invention or pharmaceutical composition according to the invention to the subject.

The invention also provides a kit of parts comprising: (a) a first pharmaceutical composition comprising a human NMT inhibitor according to the invention and a pharmaceutically acceptable carrier; and (b) a second pharmaceutical composition comprising a further therapeutic agent, suitably a further human N-myristoyl transferase inhibitor, and a pharmaceutically acceptable carrier.

DETAILED DESCRIPTION OF THE INVENTION

Figure 1:
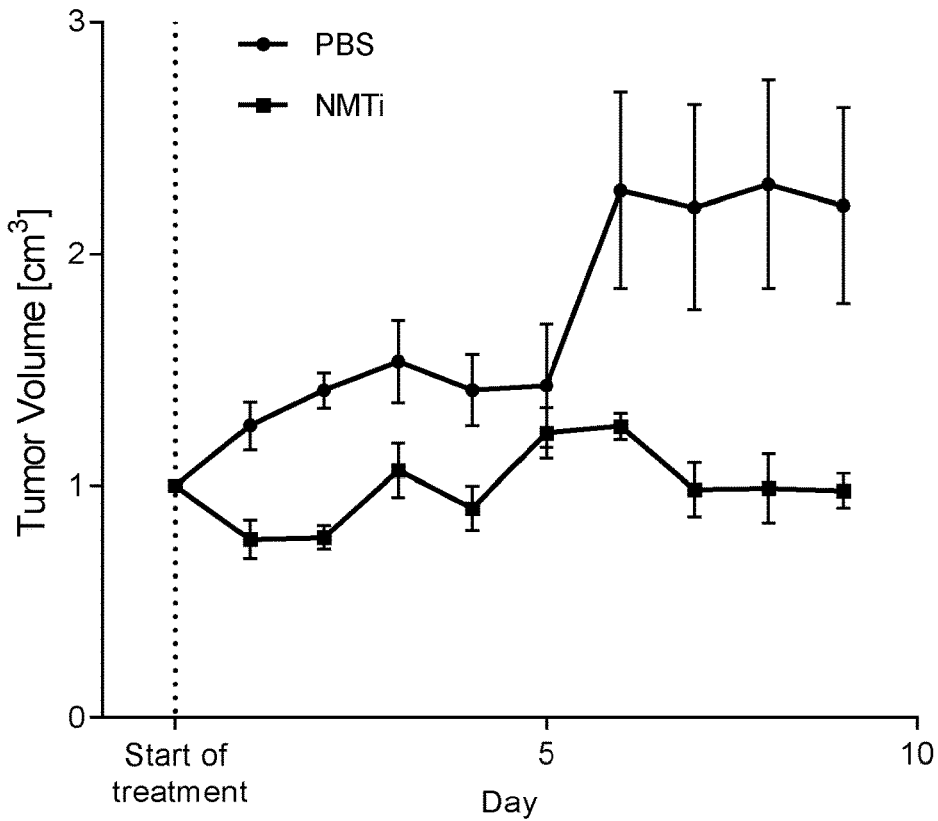
FIG. 1 shows the tumour growth rate in mice injected with MDA MB 231 cells and having a tumour of at least 50 mm3 mass treated with Example 1 ("NMTi") or control (phosphate buffered saline ("PBS")) over a 10 day period.

The invention provides a compound of formula (I), or a pharmaceutically acceptable amide, carbamate or salt thereof, including salts of such amides or carbamates,

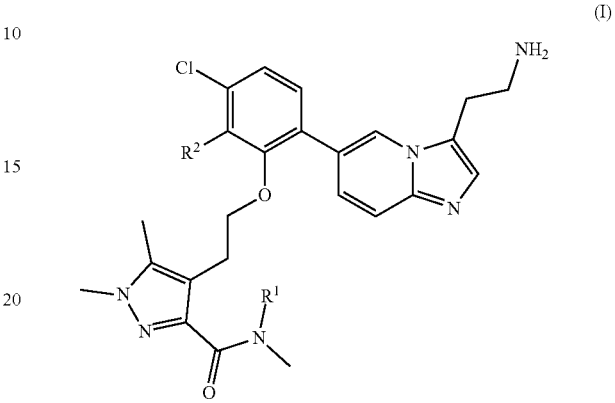

wherein $R^1$ is H or —$CH_3$; and
$R^2$ is H or F.

The compounds of the invention are NMT inhibitors.

The present inventors have found that compounds of formula (I) are highly potent inhibitors of human NMT, HsNMT1 and HsNMT2. In particular, the data in the present application shows that the compounds have a very low nanomolar $IC_{50}$ for human NMT1 (HsNMT). (It is well established that HsNMT1 and HsNMT2 are generally inhibited to the same degree by NMT inhibitor compounds (PLOS Neglected Tropical Diseases 6 (4): e1625); and the inventors are not aware of any small molecule NMT inhibitors that are selective for HsNMT2). The potency of the compounds of the invention for the HsNMT1 enzyme is so high that they have potencies at the lowest measurable threshold of the assay of Example (a). To distinguish the potency of the compounds from other NMT inhibitor compounds having $IC_{50}$ values at the threshold measurable in assay (a), compounds of the invention were tested in metabolic activity cellular assays using 4 different cancer cell lines. The tested compounds of invention had significantly lower $EC_{50}$ values in all assays compared to structurally similar comparative example compounds, and in particular 5-fluorophenyl-substituted 3-(2-aminoethyl)imidazo[1,2-a]pyridine compounds disclosed in WO2017/001812 (Imperial Innovations Limited) and taught to be active inhibitors of human NMT. As the data in WO2017/001812 teaches that chlorophenyl analogues are less active human NMT inhibitors, and less active in metabolic cellular assays, than fluorophenyl analogues having the equivalent or very similar structures, the very high potency of compounds of the invention is especially surprising.

The tested compounds of the invention, as well as being highly potent, combine this with very good metabolic stability. Examples (e), (f) and (g) below show the rat hepatocyte half-life, rat oral half-life and human liver microsomes half-life of a compound of the invention, as well as various comparative examples disclosed WO2017/001812 (Imperial Innovations Limited). From the inventors' research they believe the very potent human NMT inhibitor IMP-1088 (which is disclosed in WO2017/001812 (Imperial Innovations Limited) as compound 49), and similar potent analogues to IMP-1088, have a short in vitro and in vivo half-life, and so low metabolic stability. Thus, the very good metabolic stability of the tested compounds of the invention, combined with their high potency, is especially surprising and advantageous.

The tested compounds are also orally bioavailable, and have been shown to prevent tumour growth in mice when orally administered.

The combination of properties makes, or is expected to make, the compounds of the invention especially suitable for use as medicaments, and in particular medicaments for oral administration, for the treatment of diseases such as cancers.

In one preferred embodiment, $R^2$ is H. For example, the compound of the invention is a compound of formula (Ia):

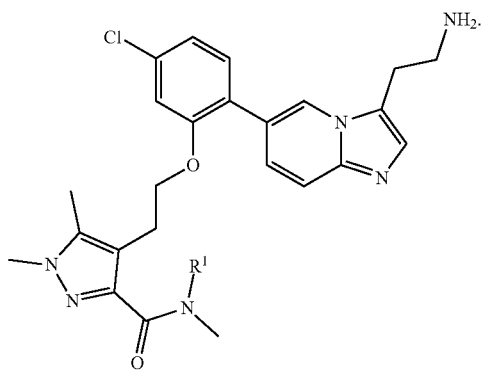

(Ia)

In embodiments where $R^2$ is H, the compound of the invention may be selected from

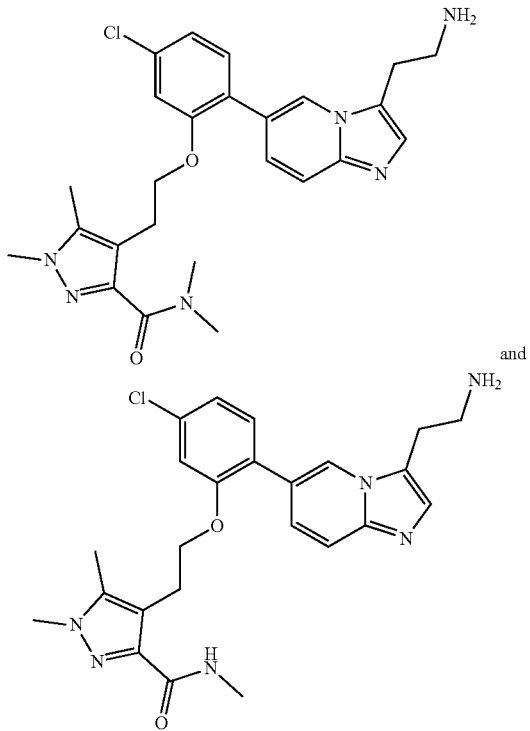

and (i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide and 4-(2-{2-[3-(2-aminoethyl)imidazo[1,2-a]pyridin-6-yl]-5-chlorophenoxy}ethyl)-N,1,5-trimethyl-1H-pyrazole-3-carboxamide).

In another embodiment of the invention, $R^2$ is F. For example, the compound of the invention is a compound of formula (Ib):

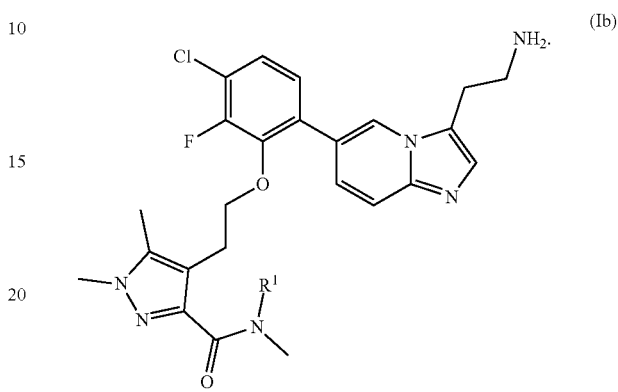

(Ib)

In embodiments where $R^2$ is F, the compound of the invention may be selected from

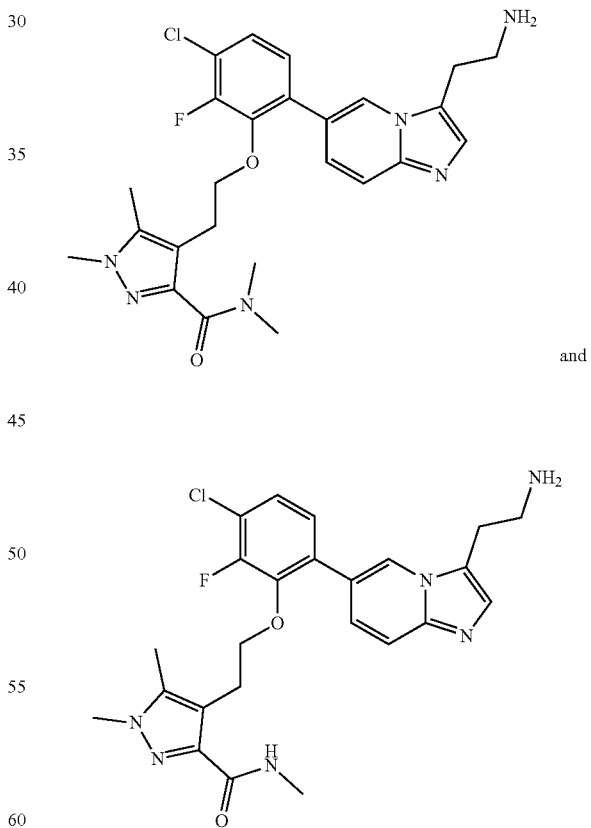

and (i.e. 4-(2-{6-[3-(2-aminoethyl)imidazo[1,2-a]pyridin-6-yl]-3-chloro-2-fluorophenoxy}ethyl)-N,N,1,5-tetramethyl-1H-pyrazole-3-carboxamide and 4-(2-{6-[3-(2-aminoethyl)imidazo[1,2-a]pyridin-6-yl]-3-chloro-4-fluorophenoxy}ethyl)-N,1,5-trimethyl-1H-pyrazole-3-carboxamide).

In one especially preferred embodiment of the invention the compound of formula (I) is

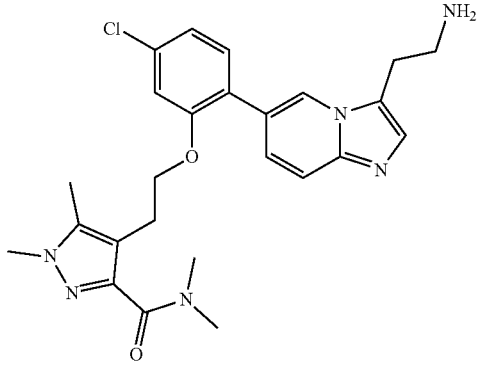 [SMILES: Cc1c(CCOc2cc(Cl)ccc2-c2ccc3ncc(CCN)n3c2)c(C(=O)N(C)C)nn1C]

or

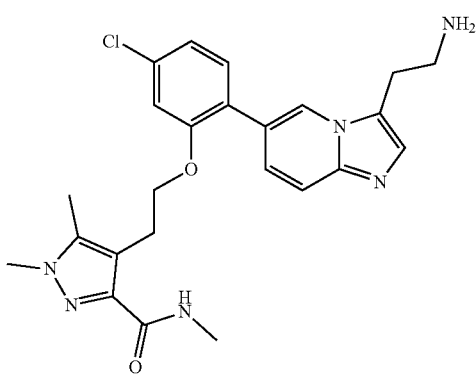

(i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide or 4-(2-{2-[3-(2-aminoethyl)imidazo[1,2-a]pyridin-6-yl]-5-chlorophenoxy}ethyl)-N,1,5-trimethyl-1H-pyrazole-3-carboxamide).

In another especially preferred embodiment of the invention the compound of formula (I) is

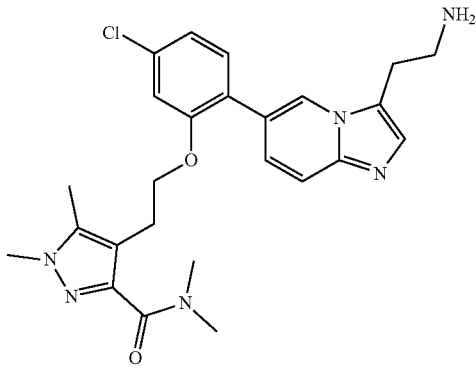

(i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide).

In another embodiment of the invention, $R^1$ is $CH_3$. In such an embodiment, the compound of formula (I) is

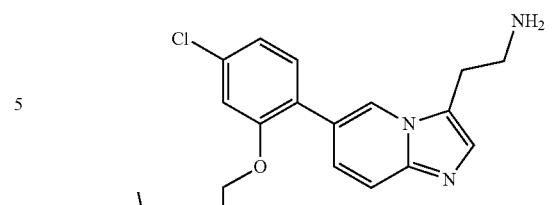

or (i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide or 4-(2-{6-[3-(2-aminoethyl)imidazo[1,2-a]pyridin-6-yl]-3-chloro-2-fluorophenoxy}ethyl)-N,N,1,5-tetramethyl-1H-pyrazole-3-carboxamide).

As shown in the Examples, compounds of formula (I) in which $R^2$ represents H appear to be more potent as inhibitors of HsNMT1 than compounds of formula (I) in which $R^2$ represents F.

Isotopic forms, for example where a hydrogen atom is replaced with deuterium, are included within the invention. Certain isotopic forms may have beneficial biological properties, for example improved metabolic stability or enhanced therapeutic activity over other isotopic forms; or a specific isotopic form may be useful for biological imaging purposes, for example carbon-11, nitrogen-13 or fluorine-18 isotopic variants may be used for positron emission tomography.

The compounds of the invention may form pharmaceutically acceptable amides, carbamates and/or salts.

Salts of compounds of the invention which are suitable for use in medicine are those wherein a counter-ion is pharmaceutically acceptable. However, salts having non-pharmaceutically acceptable counter-ions are within the scope of the present invention, for example, for use as intermediates in the preparation of the compounds of the invention and their pharmaceutically acceptable salts, and physiologically functional derivatives. By the term "physiologically functional derivative" is meant a chemical derivative of a compound of formula (I) having the same physiological function as the free compound of formula (I), for example, by being convertible in the body thereto. Amides and carbamates are examples of physiologically functional derivatives.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxy-carboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. For example, it may be the hydrochloric (HCl) salt. Other acids, which may or may not in themselves be pharmaceutically acceptable, may be useful as intermediates in obtaining the compounds of the invention and their pharmaceutical acceptable acid addition salts.

Compounds of formula (I) may have an appropriate group converted to an amide or a carbamate, and suitably to a carbamate. Typical amide and carbamate groups formed from a basic nitrogen in the compound of formula (I) include —NHC(O)$R^G$, —NHCO$_2$$R^G$, and —NHSO$_2$$R^G$, —N$R^G$C(O)$R^G$, —N$R^G$CO$_2$$R^G$, and —N$R^G$SO$_2$$R^G$ (suitably —NHCO$_2$$R^G$ and N$R^G$CO$_2$$R^G$), where $R^G$ is selected from the group consisting of $C_{1-8}$alkyl, $C_{2-8}$alkenyl, $C_{2-8}$alkynyl, $C_{3-8}$cycloalkyl and $C_{3-8}$cycloalkyl$C_{1-8}$alkyl, halo$C_{1-8}$alkyl, dihalo$C_{1-8}$alkyl, trihalo$C_{1-8}$alkyl, phenyl and phenyl$C_{1-4}$alkyl; more suitably $R^G$ is selected from the group consisting of $C_{1-8}$alkyl, $C_{2-6}$alkenyl, $C_{2-6}$alkynyl, $C_{3-8}$cycloalkyl and $C_{3-8}$cycloalkyl$C_{1-8}$alkyl most suitably $R^G$ is $C_{1-8}$alkyl (examples of is $C_{1-8}$alkyl groups include methyl, ethyl, n-propyl, iso propyl, n-butyl, t-butyl, i-butyl, sec-butyl, pentyl, 1-ethylpropyl 1-ethylbutyl, and hexyl groups). For example, a pharmaceutically acceptable carbamate of a compound of formula (I) may be tert-butyl N-[2-(6-{2-[2-(3-(dimethyl)carbamoyl-1,5-dimethyl-1H-pyrazol-4-yl)ethoxy]-4-chlorophenyl}imidazo[1,2-a]pyridin-3-yl)ethyl]-carbamate (i.e. the product of step 1 of Example 1, below), or tert-butyl N-{2-[6-(4-chloro-2-{2-[1,5-dimethyl-3-(methylcarbamoyl)-1H-pyrazol-4-yl]ethoxy}phenyl)imidazo[1,2-a]pyridin-3-yl]ethyl}carbamate (i.e. the product of step 1 of Example 2, below) or tert-butyl N-{2-[6-(4-chloro-2-{2-[3-(dimethylcarbamoyl)-1,5-dimethyl-1H-pyrazol-4-yl]ethoxy}-3-fluorophenyl)imidazo[1,2-a]pyridin-3-ylethyl}carbamate (i.e. the product of step 1 of Example 3, below) or tert-butyl N-{2-[6-(4-chloro-2-{2-[1,5-dimethyl-3-(methylcarbamoyl)-1H-pyrazol-4-yl]ethoxy}-3-fluorophenyl)imidazo[1,2-a]pyridin-3-yl]ethyl}carbamate (i.e. the product of step 1 of Example 4, below).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al., *Pharmaceutical Research*, 1995. 12 (7): p. 954-954, and Water-Insoluble Drug Formulation, $2^{nd}$ ed. R. Liu, CRC Press, page 553, which are incorporated herein by reference. Accordingly, it will be understood by the skilled person that the compounds of the invention may therefore be present in the form of solvates. Solvates of compounds of the invention which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds according to the invention.

Particularly suitable pharmaceutically acceptable derivatives of the compounds of the invention are carbamates and salts, including salts of such carbamates.

In one embodiment, the compound is not a derivative such as an amide or carbamate. In one embodiment, the compound is not a salt.

Uses of Compounds of the Invention

Inhibition of human NMT has been suggested as a target for treating or preventing various diseases or disorders, as described above. The present invention provides compounds that are NMT inhibitors. The term "NMT inhibitor" as used herein is intended to cover any moiety which binds to NMT and inhibits its activity. The inhibitors may act as competitive inhibitors, or partial competitive inhibitors. The inhibitor may bind to NMT at the myr-CoA binding pocket or at the peptide binding pocket (or inhibit NMT through another mechanism). Compounds of the invention suitably bind and inhibit NMT through the peptide binding pocket.

As the compounds of the invention are NMT inhibitors, a compound of the invention may be used in the treatment of diseases or disorders associated with NMT activity or may be used in the treatment of a disease or disorder by targeting NMT activity (for example in hyperproliferative diseases (such as cancer), and viral infections (such as picornaviral infections)). Accordingly, the present invention provides a compound according to the invention, or a pharmaceutical composition comprising a compound according to the invention and a pharmaceutically acceptable carrier, for use as a medicament. There is also provided a compound according to the invention, or a pharmaceutical composition comprising a compound according to the invention and a pharmaceutically acceptable carrier, for use in the treatment or prevention of a disease or disorder in which inhibition of N-myristoyl transferase provides a therapeutic or prophylactic effect.

The invention also provides a method for the treatment or prevention of a disease or disorder in a subject in which inhibition of N-myristoyl transferase provides a therapeutic or prophylactic effect in a subject (e.g. a mammal, for example a human), which comprises administering to the subject a therapeutically effective amount of a compound according to the invention, or a pharmaceutical composition comprising compound according to the invention and a pharmaceutically acceptable carrier.

The invention also provides the use of a compound according to the invention for the manufacture of a medicament for the treatment or prevention of a disease or disorder in which inhibition of N-myristoyl transferase provides a therapeutic or prophylactic effect.

Diseases and disorders in which inhibition of N-myristoyl transferase provides a therapeutic or prophylactic effect include: hyperproliferative disorders, viral infections, neurological diseases, ischemia, osteoporosis, diabetes, autoimmune diseases and inflammatory diseases. As such, compounds of the invention find use the treatment or prevention of those disorders/diseases.

As the compounds of the invention are especially potent inhibitors of human NMT, the compounds of the invention are expected to be especially useful in the treatment and/or prevention of viral infections (e.g. human immunodeficiency virus (HIV), human rhinovirus (HRV)) and hyperproliferative disorders (e.g. cancer), as well as other conditions for which inhibition of human NMT has been suggested as a means of therapy.

It is also expected that the compounds of the invention will find particular utility in targeting diseases in particular patient populations, i.e. where the disease is expected to be particularly affected by inhibition of N-myristoyl transferase, and especially human N-myristoyl transferase. Such diseases include hyperproliferative disorders, and especially cancer, for example a haematologic malignancy (such as a lymphoma, and in particular a B-cell lymphoma (e.g. high grade mantle zone lymphoma, follicular lymphoma, plasmablastic lymphoma, diffuse large B-cell lymphoma and Burkitt's lymphoma), a myeloma (e.g multiple myeloma) or a leukaemia (e.g. chronic lymphocytic leukaemia, AML and B-acute lymphocytic leukaemia)) or a solid-tumour (such as brain, lung, breast (e.g. triple negative breast cancer or a breast invasive carcinoma), prostate, ovary, colorectal (e.g. colon), gallbladder, kidney or liver cancer, or a neuroblastoma (for example a retinoblastoma, a glioblastoma, a small cell lung carcinoma or an astrocytoma)).

In one suitable embodiment, the compounds of the invention are for use in the treatment of a disease or disorder selected from hyperproliferative disorders and viral infections.

In one especially suitable embodiment, the compounds of the invention are for use in the treatment of a hyperproliferative disorder, wherein the hyperproliferative disorder is cancer. The cancer may be selected from the group consisting of colorectal cancer, gallbladder carcinoma, brain tumors, lymphomas (such as B-cell lymphoma (for example diffuse large B-cell lymphoma)), leukaemia (such as acute myeloid leukaemia (AML) and neuroblastoma).

The cancer may additionally, or alternatively, be a solid tumour selected from the group consisting of brain, lung, breast (e.g. triple negative breast cancer or a breast invasive carcinoma), prostate, ovary, colorectal (e.g. colon), gallbladder, kidney and liver cancer. For example, the cancer may be ovarian serous cystadenocarcinoma, esophageal carcinoma, lung squamous cell carcinoma, lung adenocarcinoma, bladder urothelial carcinoma, uterine carcinosarcoma, stomach adenocarcinoma, breast invasive carcinoma or liver hepatocellular carcinoma. In certain embodiments, the cancer is breast cancer, for example triple negative breast cancer or a breast invasive carcinoma. In certain embodiments, the cancer is brain, breast, prostate, colon, gallbladder or kidney cancer. In certain embodiments, the cancer is breast, colon or gallbladder cancer.

The cancer may additionally, or alternatively, be a haematologic malignancy selected from the group consisting of lymphoma (for example B-cell lymphoma, and in particular a lymphoma selected from the group consisting high grade mantle zone lymphoma, follicular lymphoma, plasmablastic lymphoma, diffuse large B-cell lymphoma and Burkitt's lymphoma), myeloma (for example multiple myeloma) and leukaemia (for example a leukaemia selected from the group consisting chronic lymphocytic leukaemia, AML and B-acute lymphocytic leukaemia).

The cancer may also additionally, or alternatively, be a blastoma, and in particular a neuroblastoma, for example a retinoblastoma, a glioblastoma, a small cell lung carcinoma or an astrocytoma.

In one embodiment, the cancer may be selected from the group consisting of diffuse large B-cell lymphoma, Burkitt's lymphoma, multiple myeloma, neuroblastoma, AML, and B-acute lymphocytic leukaemia. In one embodiment, the cancer may be selected from the group consisting of diffuse large B-cell lymphoma, Burkitt's lymphoma, neuroblastoma, AML, B-acute lymphocytic leukaemia and breast cancer. In another embodiment, the cancer may be selected from the group consisting of diffuse large B-cell lymphoma, neuroblastoma, B-acute lymphocytic leukaemia and triple negative breast cancer. In another embodiment, the cancer may be selected from the group consisting of colorectal cancer, gallbladder carcinoma, brain tumour, lymphoma (such as diffuse large B-cell lymphoma), leukemia (such as acute myelod leukemia) and neuroblastoma (such as retinoblastoma or glioblastoma). In another embodiment, the cancer may be selected from the group consisting of diffuse large B-cell lymphoma, Burkitt's lymphoma, multiple myeloma, neuroblastoma, AML, B-acute lymphocytic leukaemia and triple negative breast cancer. In another embodiment, the cancer may be selected from the group consisting of multiple myeloma, neuroblastoma, AML, B-acute lymphocytic leukaemia and triple negative breast cancer. In another embodiment, the cancer may be selected from the group consisting of multiple myeloma, neuroblastoma and triple negative breast cancer.

In another especially suitably embodiment, the compounds of the invention are for use in the treatment of a viral infection, and in particular an enteroviral infection or a retroviral infection. For example, the enteroviral infection may be a picornaviral infection (for example a rhinovirus, poliovirus, foot-and-mouth disease virus, coxsackievirus, hepatitis A virus or enterovirus 71 infection); and the retroviral infection may be a lentiviral infection (for example an HIV infection)). Thus the viral infection may be selected from the group consisting of a rhinovirus infection (HRV, also known as the common cold), lentivirus infection (for example HIV infection), poliovirus infection, foot-and-mouth disease virus infection, coxsackievirus infection, hepatitis A virus infection and enterovirus 71 infection. In one especially suitable embodiment, the compounds of the invention are for use in the treatment of a viral infection, wherein the viral infection is a picornaviral infection, and even more especially it is a rhinovirus infection (HRV, also known as the common cold).

The above-mentioned viral infections cause many types of diseases. For example: rhinovirus infection causes the common cold; various picornaviral infections, in particular coxsackievirus and enterovirus 71, cause hand, foot and mouth disease and polio-like syndrome; coxsackieviruses can also cause a flaccid paralysis, herpangina, acute hemorrhagic conjunctivitis, nonspecific febrile illnesses, rashes, upper respiratory tract disease, pericardial effusion, insulin-dependent diabetes (IDDM), Sjogren's syndrome, myocarditis (inflammation of the heart), pericarditis (inflammation of the sac surrounding the heart), meningitis (inflammation of the membranes that line the brain and spinal cord), and pancreatitis (inflammation of the pancreas); enterovirus 71 can also cause severe neurological diseases in children; foot-and-mouth disease virus causes foot-and-mouth disease; hepatitis A virus causes hepatitis A; and HIV infection can cause acquired immunodeficiency syndrome (AIDS). Compounds of the invention may be used in the treatment of the above-mentioned diseases caused by the viral infections mentioned above, as well as other diseases and conditions caused by an enteroviral infection or a retroviral infection.

Whilst an NMT inhibitor compound of the invention may be used as the sole active ingredient in a medicament, it is also possible for the NMT inhibitor compound to be used in combination with one or more further therapeutic agents. Accordingly, the present invention also provides a compound of the invention, together with a further therapeutic agent. The further therapeutic ingredient may be for simultaneous, sequential or separate administration. The invention also provides a kit of parts comprising: (a) a first pharmaceutical composition comprising a compound of the invention and a pharmaceutically acceptable carrier; and (b) a second pharmaceutical composition comprising a further therapeutic agent, and a pharmaceutically acceptable carrier.

Such further therapeutic agents may be further NMT inhibitors, for example a further NMT inhibitor according to the invention (i.e. a further compound of formula (I), or a pharmaceutically acceptable carbamate or salt thereof, including salts of such amides or carbamates).

The NMT inhibitor compounds of the invention can be used in combination with one or more further therapeutic agents useful for the treatment or prevention of a disease or disorder in which inhibition of N-myristoyl transferase provides a therapeutic or prophylactic effect (for example agents useful for the treatment or prevention of hyperproliferative disorders, viral infections, neurological diseases, ischemia, osteoporosis, diabetes, autoimmune diseases and inflammatory diseases, and in particular hyperproliferative disorders (e.g. cancer) and viral infections (e.g. HRV or HIV infection)). The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of a NMT inhibitor compound of the invention with other therapeutic agents useful for treating or prevention of a disease or disorder in which inhibition of N-myristoyl transferase provides a therapeutic or prophylactic effect includes in principle any combination with any pharmaceutical composition useful for treating or prevention of a disease or disorder in which inhibition of N-myristoyl transferase provides a therapeutic or prophylactic effect.

A further therapeutic agent, when employed in combination with the compounds of the invention, may be used, for example, in those amounts indicated in the Physicians' Desk Reference (PDR) for that agent, or as otherwise determined by one of ordinary skill in the art.

Where the NMT inhibitor compounds of the invention are utilized in combination with one or more further therapeutic agent(s), either concurrently or sequentially, the following combination ratios and dosage ranges are suitable: when combined with a further therapeutic agent, the NMT inhibitor compound of the invention may for example be employed in a weight ratio to the further therapeutic agent within the range from about 10:1 to about 1:10.

In one embodiment, where the NMT inhibitor compound of the invention is for the treatment or prevention of cancer, the NMT inhibitor compound of the invention may be utilized in combination with one or more further therapeutic agent(s), either concurrently or sequentially, for the treatment of cancer.

In one embodiment, where the NMT inhibitor compound of the invention is for the treatment or prevention of rhinovirus (HRV, also known as the common cold), the NMT inhibitor compound of the invention may be utilized in combination with one or more further therapeutic agent(s), either concurrently or sequentially, for the treatment of HRV and/or for the treatment of asthma and/or for the treatment of chronic obstructive pulmonary disease (COPD). For example, the further therapeutic agent(s) may be selected from the group consisting of: pleconaril, pirodavir, vapendavir BTA-798, V-073, rupintrivir, enviroxime, IFN-β (SNG001); corticosteroids (inhaled and oral, for example beclomethasone, fluticasone, budesonide, ciclesonide), beta agonists (for example salbutamol, levosalbutamol, terbutaline, pirbuterol, procaterol, clenbuterol, metaproterenol, fenoterol, bitolterol mesylate, ritodrine, isoprenaline, salmeterol, formoterol, bambuterol, clenbuterol, olodaterol and indacaterol) muscarinic antagonists (for example ipratropium and diphenhydramine), leukotriene receptor antagonists (for example montelukast, zafirlukast, zileuton), cromylins, PDE4 inhibitors (for example ibudilast), and anti-cytokine antibodies, such as anti-IgE (for example omalizumab), anti-IL5 (for example mepolizumab, reslizumab and benralizumab) anti-IL4 (for example dupilumab and pitrakinra).

In one embodiment, the compound of the invention comprises an isotope atom, suitably a radioactive isotope atom. As defined herein, an isotope atom is an atom of an element that is not the most common naturally occurring isotope. Such compounds may find use as diagnostic agents for the diagnosis of a disease or disorder in which inhibition of NMT provides a therapeutic or prophylactic effect. Accordingly, the present invention also provides the use of a compound of the invention comprising an isotope atom, suitably a radioactive isotope atom, as a diagnostic agent for the diagnosis of a disease or disorder in which inhibition of NMT provides a therapeutic or prophylactic effect.

Doses and Formulations

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Due to the high potency of the compounds of the invention as NMT inhibitors and the good pharmacokinetic properties (e.g. the long half-life) of at least the tested compounds, a compound of the present invention may generally be provided in a lower total dosage and/or dosed less frequently than other known NMT inhibitors.

Advantageously, compounds of the invention may be administered in a single daily dose, or the total daily dosage may be administered in divided doses two, three or four times daily.

Oral dosages of the present invention, when used for the indicated effects, will range between about 0.01 mg per kg of body weight per day (mg/kg/day) to about 100 mg/kg/day, suitably 0.01 mg per kg of body weight per day (mg/kg/day) to 10 mg/kg/day, and most suitably 0.1 to 5.0 mg/kg/day, for adult humans. For oral administration, the compositions are suitably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, suitably from about 1 mg to about 100 mg of active ingredient. Intravenously, the most suitable doses will range from about 0.1 to about 10 mg/kg/minute during a constant rate infusion. Advantageously, compounds of the invention may be administered in a single daily dose, or the total daily dosage may be administered in divided doses of two, three or four times daily. Furthermore, suitably compounds of the invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), intranasal (also known as nasal administration), inhalation (including fine particle dusts or mists which may be generated by means of various types of metered dose pressurized aerosols, nebulizers or insufflators) insufflation, rectal, intraperitoneal and topical (including dermal, buccal, sublingual, and intraocular) administration, although the most suitable route may depend upon, for example, the condition and disorder of the recipient.

Suitable pharmaceutical formulations according to the invention are those suitable for oral and parenteral administration; and more suitably are those suitable for oral administration. Such embodiments are especially suitable for, for example, the treatment of a hyperproliferative disorder, and in particular a cancer.

In another suitable embodiment a compound according to the present invention is administered by intranasal, inhalation (including fine particle dusts or mists which may be generated by means of various types of metered dose pressurized aerosols, nebulizers or insufflators) or insufflation administration. Such embodiments are especially suitable for, for example, the treatment of a picornaviral infection, such as human rhinovirus infection. Such a method of administration allows for low doses of the compound of the invention to be administered, which can lead to a reduction in side-effects. For example, a daily dose of 10 to 0.01 µg, suitably 1 to 0.01 µg, and more suitably in the region of as low as 0.1 µg (100 ng) of compound of the invention may be used.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The compounds of the invention can, for example, be administered in a form suitable for immediate release or extended release. Immediate release or extended release can be achieved by the use of suitable pharmaceutical compositions comprising a compound of the present invention, or, particularly in the case of extended release, by the use of devices such as subcutaneous implants or osmotic pumps. The compounds of the invention may also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds according to the invention can also be delivered through the oral cavity by sublingual and/or buccal administration. Molded tablets, compressed tablets or freeze-dried tablets are exemplary forms which may be used. Exemplary compositions include those formulating a compound of the present invention with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for intranasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Suitable unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Synthesis of Compounds of the Invention

Numerous synthetic routes to the compounds of the invention can be devised by a person skilled in the art and the exemplified synthetic routes described below do not limit the invention. Many methods exist in the literature for the synthesis of heterocycles, for example: Joule, J. A.; Mills, K., Heterocyclic Chemistry, 2010, 5th Edition, Pub. Wiley. A number of possible synthetic routes are exemplified below. Where appropriate, any initially produced compound according to the invention can be converted into another compound according to the invention by known methods.

General Method I

The invention provides a process for the preparation of a compound of formula (I), the process comprising:

(i) subjecting a compound of formula (II)

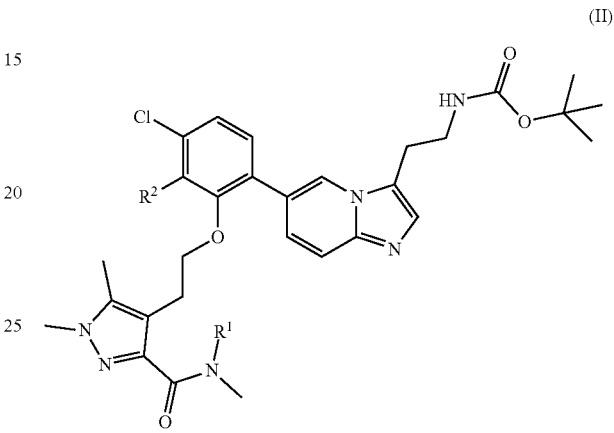

(II)

wherein $R^1$ is H or —$CH_3$; and
$R^2$ is H or F; to deprotection conditions to produce a compound of formula (I), and (ii) optionally converting the compound of formula (I) to a pharmaceutically acceptable amide, carbamate or salt thereof, including salts of such amides or carbamates.

The step of subjecting the compound of formula (II) to deprotection conditions to produce a compound of formula (I) may comprise contacting the compound of formula (II) with an acid (e.g. HCl).

The compound of formula (II) may, for example, be produced by reaction of a compound of formula (III)

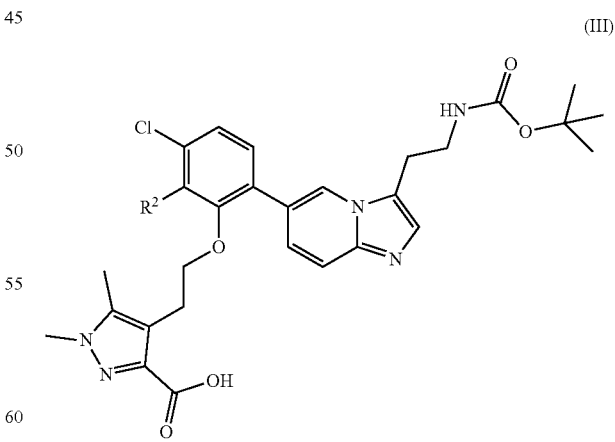

(III)

wherein $R^2$ is H or F;
with methylamine or dimethylamine in the presence of a base such as triethylamine and a coupling agent (e.g. 1-ethyl-3-(3-dimethylaminopropyl) carbodiimide (EDCI)).

The compound of formula (III) may for example be produced by reaction of a compound of formula (IV)

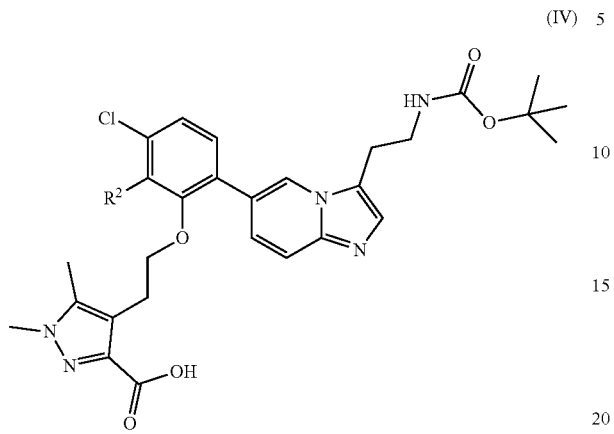

wherein R² is H or F;
under hydrolysis conditions, e.g. lithium hydroxide in THF/water.

The compound of formula (IV) may for example be produced by reacting a compound of formula (V)

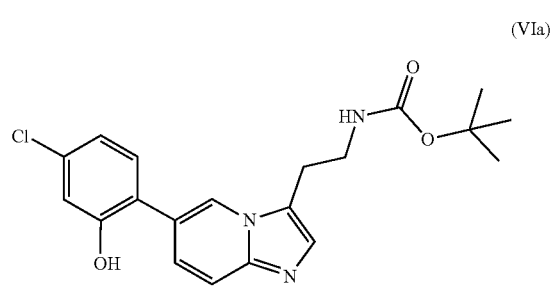

with a compound of formula (VIa) or (VIb)

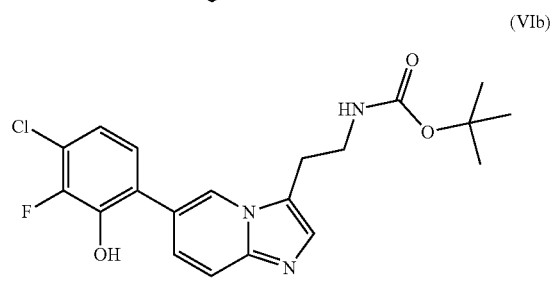

using a Mitsunobu coupling agent such as (cyanomethylene)tributylphosphorane (CMBP).

The compound of formula (VIa) may for example be produced by reacting a compound of formula (VII)

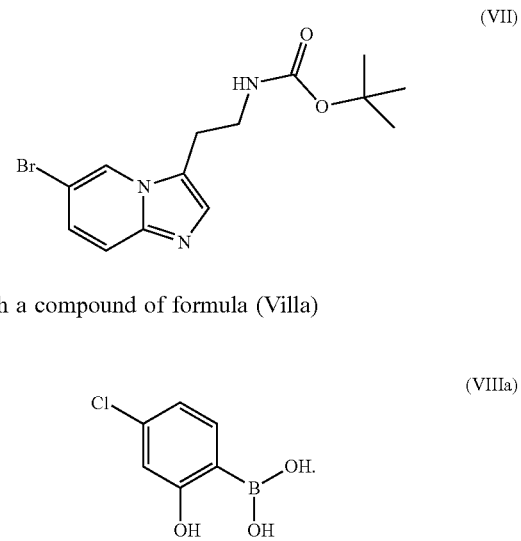

with a compound of formula (VIIIa)

The compound of formula (VIb) may for example be produced by reacting a compound of formula (VII)

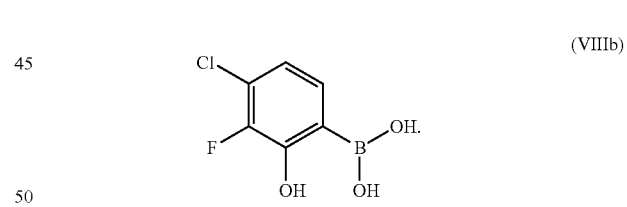

with a compound of formula (VIIIb)

EXAMPLES

Synthesis of Example Compounds
General Experimental Details
LC-MS

Compounds requiring purification under basic conditions were purified on an LC-MS system equipped with a YMC Actus Triart C18 5 μm (20×250 mm) column or Gemini NX 5 μm C18 (100×30 mm) column, using a gradient elution of acetonitrile in water containing 20 mM Ammonium bicarbonate (10-45% over 30 min then 95% acetonitrile for 2 minutes).

Hplc

The purity of Examples Compound 1 and 2 was determined by analytical hplc using an Eclipse Extend 5 μm C18

(150×4.6 mm) or Shimadzu L Column 2 ODS 5 μm C18 (150×4.6 mm) column using gradient elution of acetonitrile in water containing 10 mM ammonium acetate over 12 min.
NMR $^1$H NMR and $^{13}$C spectra were recorded on 400 MHz and 101 MHz respectively instruments at room temperature unless specified otherwise were referenced to residual solvent signals. Data are presented as follows: chemical shift in ppm, integration, multiplicity (br=broad, app=apparent, s=singlet, d=doublet, t=triplet, q=quartet, p=pentet, m=multiplet) and coupling constants in Hz.

General Procedures
Boc Deprotection (Method B)

The Boc protected amine was dissolved in dioxane and treated with a solution of HCl in dioxane (6M, 2 mL). The reaction mixture was stirred at room temperature overnight. All volatiles were removed under reduced pressure and the product triturated with ether redissolved in water and freeze dried.

Preparation of Starting Materials

All of the starting materials for making the intermediate and example compound were obtained from commercial sources or using literature methods, except for methyl 4-(2-hydroxyethyl)-1,5-dimethyl-1H-pyrazole-3-carboxylate, which was made as follows:

Preparation of methyl 4-(2-hydroxyethyl)-1,5-dimethyl-1H-pyrazole-3-carboxylate starting material

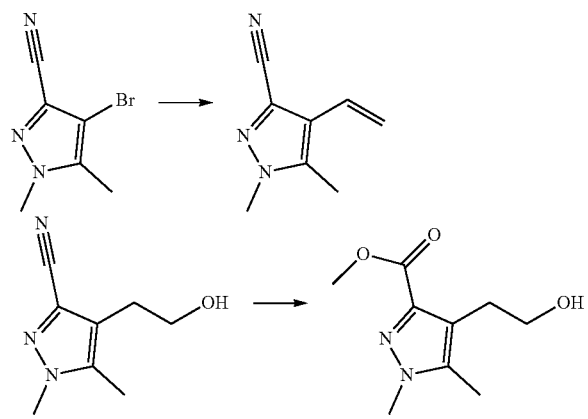

Step 1

A solution of 4-bromo-1,5-dimethyl-1H-pyrazole-carbonitrile (8.0 g, 40 mmol) in dry DMF (40 mL) was treated with tributylvinylstannane (23.4 mL, 80 mmol). The mixture was purged with argon for 15 min before addition of tetrakis(triphenylphosphine) palladium (0) (2.3 g, 2 mmol). The reaction was heated to 110° C. overnight, diluted with ethyl acetate and washed with potassium fluoride solution, water and brine, dried over $Na_2SO_4$, concentrated under reduced pressure. The crude product was purified by flash column chromatography by elution with ethylacetate/hexane (20:80) to provide 4-ethenyl-1,5-dimethyl-1H-pyrazole-3-carbonitrile (4.0 g, 68%). $^1$H NMR (400 MHZ, $CDCl_3$) 6.45 (dd, 1H), 5.80 (dd, 1H), 5.34 (dd, 1H), 3.82 (s, 3H), 2.29 (s, 3H).

Step 2

A solution of 4-ethenyl-1,5-dimethyl-1H-pyrazole-3-carbonitrile (1.2 g, 8.2 mmol) in dioxane (5 mL) was treated with a solution of 9-BBN (0.5M in THF, 32 mL, 16 mmol) under a nitrogen atmosphere. The reaction was heated to 100° C. overnight. The mixture was re-cooled to 0° C., and was treated with ethanol (4.8 mL), NaOH solution (6M, 2.4 mL), $H_2O_2$ (50% solution, 3.6 mL). The reaction mixture was heated at RT for 2 hr diluted with DCM/methanol (95:5), dried over sodium sulphate and concentrated under reduced pressure. The crude product purified by flash column chromatography by elution with DCM/methanol (98:2) to provide the title compound 4-(2-hydroxyethyl)-1,5-dimethyl-1H-pyrazole-3-carbonitrile (500 mg, 37%). 1H NMR (400 MHZ, $CDCl_3$) 3.81 (s, 3H), 3.78 (q, 2H), 2.74 (t, 2H), 2.55 (s, 3H), 1.86 (t, 1H).

Step 3

A solution of 4-(2-hydroxyethyl)-1,5-dimethyl-1H-pyrazole-3-carbonitrile (1.0 g, 6.1 mmol) in methanol (12 mL) was treated with a solution of HCl in dioxane (4M, 12 mL). The reaction mixture was stirred at 80° C. for 5 hr and evaporated under reduced pressure. The crude product was basified with sat. $NaHCO_3$ solution and diluted with EtOAc, washed with water, brine, dried over sodium sulfate and evaporated under reduced pressure to give methyl 4-(2-hydroxyethyl)-1,5-dimethyl-1H-pyrazole-3-carboxylate (1.1 g, 92%). $^1$H NMR (400 MHZ, $CDCl_3$) 3.90 (s, 3H), 3.84 (s, 3H), 3.77 (q, 2H), 2.93 (t, 2H), 2.23 (s, 3H), 2.07 (t, 1H).

Preparation of Intermediate 1
Intermediate 1

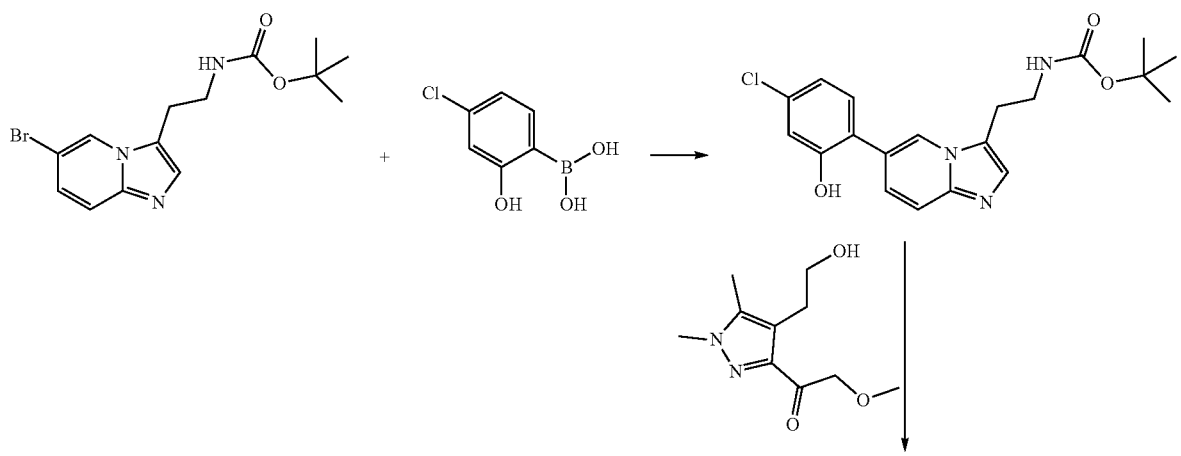

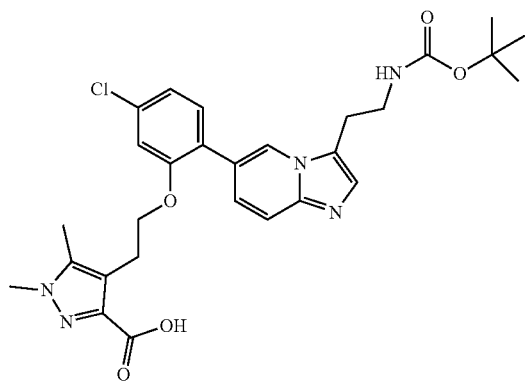
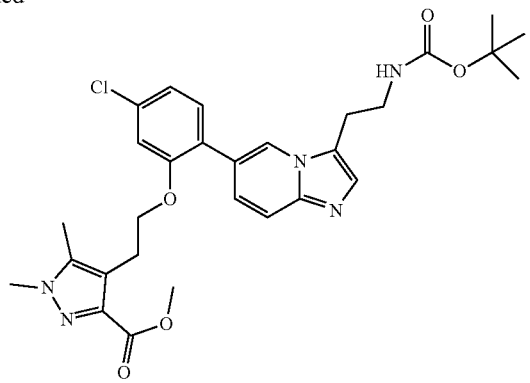

4-(2-{2-[3-(2-{(tert-butoxy)carbonyl]amino}ethyl)imidazo[1,2-a]pyridin-6-yl]-5-chlorophenoxy}ethyl)-1,5-dimethyl-1H-pyrazole-3-carboxylic acid Step 1

A solution of tert-butyl N-(2-{6-bromoimidazo[1,2-a]pyridin-3-yl} ethyl) carbamate (7.0 g, 20.5 mmol) was dissolved in dioxane/water (5:1, 175 mL) and treated with 4-chloro-2-hydroxybenzene boronic acid (8.0 g, 46.3 mmol) and tetrakis(triphenylphosphine) palladium (0) (937 mg, 2.0 mmol), followed by potassium phosphate (13 g, 61.7 mmol). The reaction mixture was purged with argon then heated to 100° C. for 3 hr, cooled to room temperature and filtered through a bed of Celite and washed with ethyl acetate. The ethyl acetate layer taken dried over Na$_2$SO$_4$, and evaporated under reduced pressure. The crude product was purified by column chromatography eluting with 3% MeOH in DCM to give tert-butyl N-{2-[6-(4-chloro-2-hydroxyphenyl)imidazo[1,2-a]pyridin-3-yl]ethyl}carbamate (7.98 g, 97%). $^1$H NMR (400 MHZ, DMSO-d$_6$) δ 8.49 (s, 1H), 7.43-7.62 (m, 4H), 6.97-7.01 (m, 3H), 5.76 (s, 1H), 3.27 (t, 2H), 3.05 (t, 2H), 1.34 (s, 9H).

Step 2

A solution of methyl tert-butyl N-{2-[6-(4-chloro-2-hydroxyphenyl)imidazo[1,2-a]pyridin-3-yl] ethyl}carbamate (5.0 g, 12.9 mmol) in toluene (50 mL) was reacted with methyl 4-(2-hydroxyethyl)-1,5-dimethyl-1H-pyrazole-3-carboxylate (3.07 g, 15.5 mmol) and cyanomethylene tributylphosphorane (6.77 mL, 25.8 mmol) at 100° C. for 16 hr. The reaction mixture was then diluted with ethyl acetate, and washed with water and brine, dried over Na$_2$SO$_4$ and concentrated. This crude material was purified by column chromatography by elution with DCM:methanol (95:5) to give methyl 4-(2-{2-[3-(2-{[(tert-butoxy)carbonyl]amino}ethyl)imidazo[1,2-a]pyridin-6-yl]-5-chlorophenoxy}ethyl)-1,5-dimethyl-1H-pyrazole-3-carboxylate (3.8 g, 52%) as a brown gum. $^1$H NMR (400 MHZ, DMSO-d$_6$) δ 8.39 (s, 1H), 7.53 (d, 1H), 7.45 (s, 1H), 7.43 (d, 1H), 7.24-7.27 (m, 2H), 7.11 (dd, 1H), 6.97 (br, t, 1H), 5.75 (s, 1H), 4.14 (t, 2H), 3.71 (s, 3H), 3.68 (s, 3H), 2.99-3.03 (m, 4H), 1.91 (s, 3H), 1.30 (s, 9H).

Step 3

A solution of methyl 4-(2-{2-[3-(2-{[(tert-butoxy)carbonyl]amino}ethyl)imidazo[1,2-a]pyridin-6-yl]-5-chlorophenoxy}ethyl)-1,5-dimethyl-1H-pyrazole-3-carboxylate (3.0 g, 5.3 mmol) in THF-water (4:1, 50 mL) was treated with methanol (0.1 mL) followed by lithium hydroxide hydrate (444 mg, 10.6 mmol). The resulting mixture was stirred at rt for 16 hr. The reaction mixture was cooled to 0° C. and was acidified with saturated citric acid solution and extracted with DCM. The final organic layer was dried over sodium sulphate and concentrated to afford desired product 4-(2-{2-[3-(2-{[(tert-butoxy)carbonyl]amino}ethyl)imidazo[1,2-a]pyridin-6-yl]-5-chlorophenoxy}ethyl)-1,5-dimethyl-1H-pyrazole-3-carboxylic acid (2.7 g, 92%) as a brown solid. $^1$H NMR (400 MHZ, DMSO-d$_6$) δ 8.42 (s, 1H), 7.56 (d, 1H), 7.44-7.55 (m, 2H), 7.32 (d, 1H), 7.27 (s, 1H), 7.11 (d, 1H), 6.98 (m, 1H), 5.76 (s, 1H), 4.13 (t, 2H), 3.68 (s, 3H), 3.32 (t, 2H), 3.01-3.04 (m, 4H), 1.93 (s, 3H), 1.29 (s, 9H).

Intermediate 2

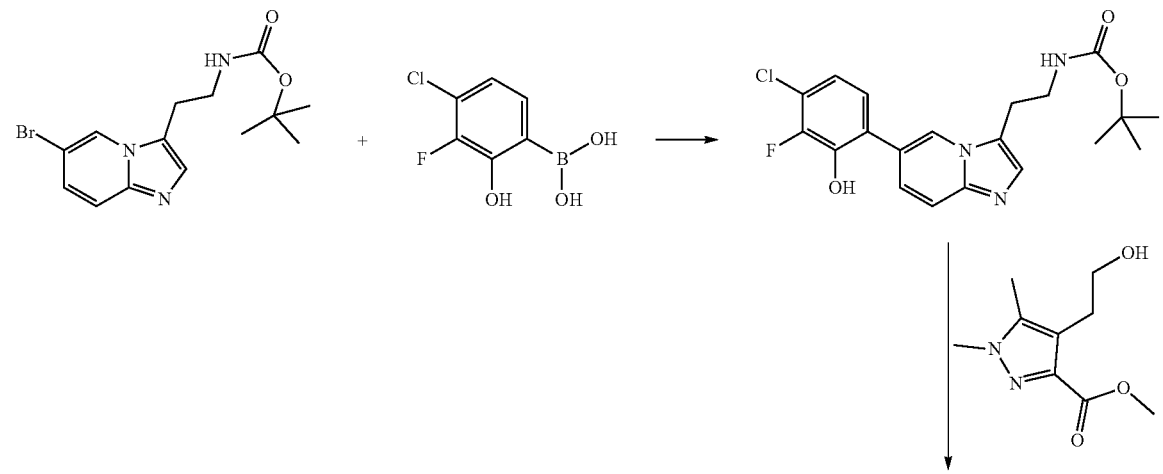

-continued

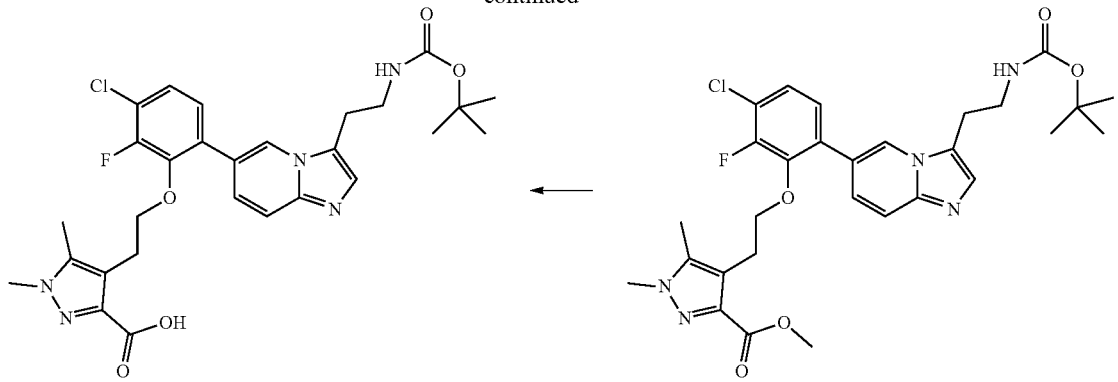

4-(2-{6-[3-(2-{[(tert-butoxy)carbonyl]amino}ethyl)imidazo[1,2-a]pyridin-6-yl]-3-chloro-2-fluorophenoxy}ethyl)-1,5-dimethyl-1H-pyrazole-3-carboxylic acid Step 1

A solution of tert-butyl N-(2-{6-bromoimidazo[1,2-a]pyridin-3-yl} ethyl) carbamate (1.0 g, 2.9 mmol) was dissolved in dioxane/water (10:1, 11 mL) and treated with 4-chloro-3-fluoro-2-hydroxybenzene boronic acid (1.68 g, 8.8 mmol) and tetrakis(triphenylphosphine) palladium (0) (340 mg, 0.29 mmol), followed by potassium phosphate (1.87 g, 8.8 mmol). The reaction mixture was purged with argon then heated to 100° C. for 5 hr, cooled to room temperature and filtered through a bed of Celite and washed with water and DCM. The organic layer was washed with water (20 mL), brine (20 mL) dried over Na$_2$SO$_4$, and evaporated under reduced pressure. The crude product was purified by column chromatography eluting with 4% MeOH in DCM to give tert-butyl N-{2-[6-(4-chloro-3-fluoro-2-hydroxyphenyl)-1H,8aH-imidazo[1,2-a]pyridin-3-yl]ethyl}carbamate (600 mg, 50%) as a brown solid. $^1$H NMR (400 MHZ, DMSO-d$_6$) δ 8.42 (s, 1H), 7.57 (d, 1H), 7.41 (d, 1H), 7.39 (d, 1H), 7.28 (d, 1H), 7.11 (t, 1H), 6.98 (dd, 1H), 3.30 (t, 2H), 3.03 (t, 2H), 1.30 (s, 9H).

Step 2

A solution of tert-butyl N-{2-[6-(4-chloro-3-fluoro-2-hydroxyphenyl)-1H,8aH-imidazo[1,2-a]pyridin-3-yl]ethyl}carbamate (900 mg, 2.2 mmol) in toluene (15 mL) was reacted with methyl 4-(2-hydroxyethyl)-1,5-dimethyl-1H-pyrazole-3-carboxylate (440 mg, 15.5 mmol) and cyanomethylene tributylphosphorane (1.2 mL, 4.4 mmol) at 100° C. for 16 hr. The reaction mixture was then diluted with ethyl acetate, and washed with water and brine, dried over Na$_2$SO$_4$ and concentrated. This crude material was purified by column chromatography by elution with DCM:methanol (95:5) to give methyl 4-(2-{6-[3-(2-{[(tert-butoxy)carbonyl]amino}ethyl)imidazo[1,2-a]pyridin-6-yl]-3-chloro-2-fluorophenoxy}ethyl)-1,5-dimethyl-1H-pyrazole-3-carboxylate; (700 mg, 46%) as a brown gum. $^1$H NMR (400 MHZ, DMSO-d$_6$) 12.4 (s, 1H), 8.41 (s, 1H), 7.54 (d, 1H), 7.45 (s, 1H), 7.40 (d, 1H), 7.35 (d, 1H), 7.31 (d, 1H), 6.98 (t, 1H), 5.76 (s, 1H), 4.00 (t, 2H), 3.64 (s, 3H), 3.03 (t, 2H), 2.88 (t, 2H), 1.91 (s, 3H), 1.29 (s, 9H).

Step 3

A solution of methyl 4-(2-{6-[3-(2-{[(tert-butoxy)carbonyl]amino}ethyl)imidazo[1,2-a]pyridin-6-yl]-3-chloro-2-fluorophenoxy}ethyl)-1,5-dimethyl-1H-pyrazole-3-carboxylate (700 mg, 1.2 mmol) in THF-water (4:1, 12 mL) was treated with methanol (0.1 mL) followed by lithium hydroxide hydrate (100 mg, 2.4 mmol). The resulting mixture was stirred at rt for 16 hr. The reaction mixture was cooled to 0° C. and was acidified with saturated citric acid solution and extracted with DCM. The final organic layer was dried over sodium sulphate and concentrated to afford desired product 4-(2-{6-[3-(2-{[(tert-butoxy)carbonyl]amino}ethyl)imidazo[1,2-a]pyridin-6-yl]-3-chloro-2-fluorophenoxy}ethyl)-1,5-dimethyl-1H-pyrazole-3-carboxylic acid (550 mg, 80%). $^1$H NMR (400 MHZ, DMSO-d$_6$) δ 8.42 (s, 1H), 7.56 (d, 1H), 7.44-7.55 (m, 2H), 7.32 (d, 1H), 7.27 (s, 1H), 7.11 (d, 1H), 6.98 (m, 1H), 5.76 (s, 1H), 4.13 (t, 2H), 3.68 (s, 3H), 3.32 (t, 2H), 3.01-3.04 (m, 4H), 1.93 (s, 3H), 1.29 (s, 9H).

Preparation of Examples 1-4:

Example 1

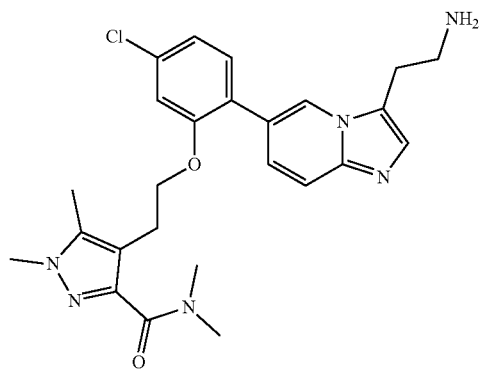 [SMILES: Cc1c(CCOc2cc(Cl)ccc2-c2ccc3ncc(CCN)n3c2)c(C(=O)N(C)C)nn1C]

4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide Step 1

A solution of 4-(2-{2-[3-({[2-(tert-butoxy)carbonyl]amino}ethyl)imidazo[1,2-a]pyridin-6-yl]-4-chlorophenoxy}ethyl)-1,5-dimethyl-1H-pyrazole-3-carboxylic acid (Intermediate 1, 1.8 g, 3.25 mmol) in THF (20 mL) was added carbonyldimidazole (790 mg, 4.9 mmol) and the reaction mixture was stirred at rt for 3 hr. The mixture was treated with triethylamine (1.4 mL, 9.7 mmol) followed by dimethylamine solution (2M in THF, 3.2 mL, 6.5 mmol).

The reaction mixture was stirred at rt for 16 hrs, quenched by addition of saturated sodium bicarbonate solution, extracted with ethyl acetate. The organic extract was dried over sodium sulphate and concentrated. The crude product was purified by prep TLC (3% MeOH/DCM) to give tert-butyl N-[2-(6-{2-[2-(3-(dimethyl) carbamoyl-1,5-dimethyl-1H-pyrazol-4-yl)ethoxy]-4-chlorophenyl}imidazo[1,2-a]pyridin-3-yl)ethyl]-carbamate as an off-white solid (1.0 g, 53%). $^1$H NMR (400 MHz, DMSO-$d_6$) δ 8.38 (s, 1H), 7.51 (d, 1H), 7.42-7.45 (m, 2H), 7.23-7.26 (m, 2H), 7.11 (dd, 1H), 6.98 (m, 1H), 5.76 (s, 1H), 4.12 (t, 2H), 3.65 (s, 3H), 3.36 (t, 2H), 3.03 (s, 3H), 3.00 (t, 2H), 2.90 (s, 3H), 2.84 (t, 2H), 1.95 (s, 3H), 1.29 (d, 9H).

Step 2

According to the general method for Boc deprotection (method A) tert-butyl N-[2-(6-{2-[2-(3-(dimethyl) carbamoyl-1,5-dimethyl-1H-pyrazol-4-yl)ethoxy]-4-chlorophenyl}imidazo[1,2-a]pyridin-3-yl)ethyl]-carbamate (1.40 g, 2.4 mmol) was treated with a solution of HCl in ether (2M, 70 mL). The solution stirred at room temperature for 3 hr and was evaporated under reduced pressure. The crude product dissolved in water and freeze dried to give the title compound as an off white solid (1.23 g, 92%) hplc rt 6.3 min LC-MS MH$^+$ 481; 1H NMR (400 MHZ, DMSO-$d_6$) δ 14.9 (br.s, 1H), 9.01 (s, 1H), 8.36 (br. s, 3H), 8.17 (s, 1H), 8.02 (dd, 2H), 7.55 (d, 1H), 7.32 (d, 1H), 7.17 (d, 1H), 4.14 (t, 2H), 3.70 (s, 3H), 3.48 (t, 2H), 3.19 (t, 2H), 3.07 (s, 3H), 2.91 (s, 3H), 2.86 (t, 2H), 2.07 (s, 3H).

Example 2

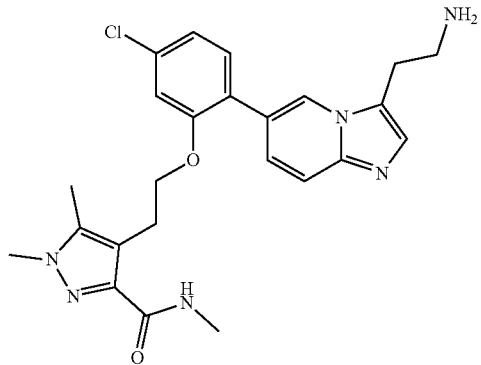

4-(2-{2-[3-(2-aminoethyl)imidazo[1,2-a]pyridin-6-yl]-5-chlorophenoxy}ethyl)-N,1,5-trimethyl-1H-pyrazole-3-carboxamide Step 1

A solution of 4-(2-{2-[3-(2-{[(tert-butoxy)carbonyl]amino}ethyl)imidazo[1,2-a]pyridin-6-yl]-4-chlorophenoxy}ethyl)-1,5-dimethyl-1H-pyrazole-3-carboxylic acid (Intermediate 1, 64 mg, 0.19 mmol) in THF (2 mL) was treated with triethylamine (0.048 mL, 0.35 mmol), methylamine solution (2M in THF, 0.17 mL, 0.35 mmol), hydroxybenztriazole (23.4 mg, 0.17 mmol) and EDCI (33.2 mg, 0.17 mmol). The reaction mixture was stirred at rt for 16 hrs, quenched with saturated NaHCO$_3$, extracted with ethyl acetate. The combined extracts were washed with water and brine, dried over sodium sulphate and concentrated. The crude product was purified by prep TLC (5% MeOH/DCM) to give tert-butyl N-{2-[6-(4-chloro-2-{2-[1,5-dimethyl-3-(methylcarbamoyl)-1H-pyrazol-4-yl]ethoxy}phenyl)imidazo[1,2-a]pyridin-3-yl]ethyl}carbamate as an off-white solid (30 mg, 46%). $^1$H NMR (400 MHZ, DMSO-$d_6$) δ 8.37 (s, 1H), 7.90 (d, 1H), 7.52 (d, 1H), 7.42-7.45 (m, 2H), 7.23-7.27 (m, 2H), 7.09 (d, 1H), 6.98 (t, 1H), 5.75 (s, 1H), 4.16 (t, 2H), 4.02 (q, 1H), 3.66 (s, 3H), 3.31 (t, 2H), 3.01 (m, 4H), 2.68 (s, 3H), 1.90 (s, 3H), 1.30 (d, 9H).

Step 2

According to the general method for Boc deprotection (method B) tert-butyl N-{2-[6-(4-chloro-2-{2-[1,5-dimethyl-3-(methylcarbamoyl)-1H-pyrazol-4-yl]ethoxy}phenyl)imidazo[1,2-a]pyridin-3-yl]ethyl}carbamate (30 mg, 0.053 mmol) was dissolved in dioxane (2 mL), cooled to 0° C. and treated with a solution of HCl in ether (2M, 2 mL). The solution stirred at room temperature for 3 hr and was evaporated under reduced pressure. The crude product dissolved in water and freeze dried to give the title compound as a light brown solid (20 mg, 81%) hplc rt 3.9 min LC-MS MH$^+$ 467; 1H NMR (400 MHZ, DMSO-$d_6$) δ 14.7 (br.s, 1H), 8.98 (s, 1H), 8.19 (br. s, 3H), 8.15 (s, 1H), 8.05 (d, 1H), 8.01 (d, 1H), 7.89 (q, 1H), 7.55 (dd, 1H), 7.37 (d, 1H), 7.19 (dd, 1H), 4.18 (t, 2H), 3.72 (s, 3H), 3.46 (t, 2H), 3.20 (q, 2H), 3.04 (t, 2H), 2.67 (d, 3H), 2.07 (s, 3H).

Example 3

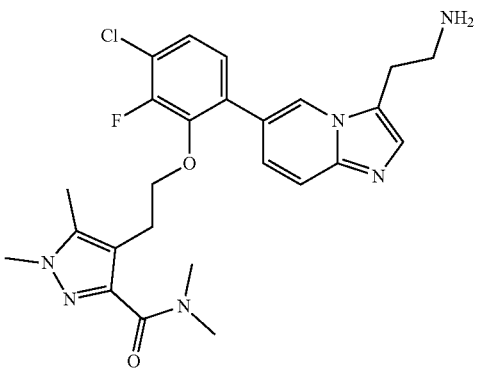 [SMILES: Cc1c(CCOc2c(-c3ccc4ncc(CCN)n4c3)ccc(Cl)c2F)c(C(=O)N(C)C)nn1C]

4-(2-{6-[3-(2-aminoethyl)imidazo[1,2-a]pyridin-6-yl]-3-chloro-2-fluorophenoxy}ethyl)-N,N,1,5-tetramethyl-1H-pyrazole-3-carboxamide Step 1

A solution of 4-(2-{6-[3-(2-{[(tert-butoxy)carbonyl]amino}ethyl)imidazo[1,2-a]pyridin-6-yl]-3-chloro-2-fluorophenoxy}ethyl)-1,5-dimethyl-1H-pyrazole-3-carboxylic acid (Intermediate 2, 250 mg, 0.44 mmol) in THF (2 mL) was added dimethylamine (2M, in THF, 0.66 mL, 1.31 mmol) followed by triethylamine (0.31 mL, 2.18 mmol), EDC hydrochloride (125 mg, 0.66 mmol) and hydroxybenztriazole (88 mg, 0.66 mmol) and the reaction mixture was stirred at rt for 2 days. The reaction mixture was quenched by addition of saturated sodium bicarbonate solution, extracted with ethyl acetate. The organic extract was washed with water, brine, dried over sodium sulphate and concentrated. The crude product was purified by prep TLC (3% MeOH/DCM) to give tert-butyl N-{2-[6-(4-chloro-2-{2-[3-(dimethylcarbamoyl)-1,5-dimethyl-1H-pyrazol-4-yl]ethoxy}-3-fluorophenyl)imidazo[1,2-a]pyridin-3-yl]ethyl}carbamate (100 mg, 38%). $^1$H NMR (400 MHZ, DMSO-$d_6$) δ 8.41 (s, 1H), 7.52 (d, 1H), 7.44 (s, 1H), 7.40

(d, 1H), 7.36 (d, 1H), 7.27 (d, 1H), 6.98 (dd, 1H), 3.95 (t, 2H), 3.62 (s, 3H), 3.28 (t, 2H), 3.03 (t, 2H), 2.94 (s, 3H), 2.84 (s, 3H), 2.71 (t, 2H), 1.93 (s, 3H), 1.30 (d, 9H).

Step 2

According to the general method for Boc deprotection (method A) tert-butyl N-{2-[6-(4-chloro-2-{2-[3-(dimethylcarbamoyl)-1,5-dimethyl-1H-pyrazol-4-yl]ethoxy}-3-fluorophenyl)imidazo[1,2-a]pyridin-3-yl]ethyl}carbamate (100 mg, 01.7 mmol) was dissolved in ether (2 mL) and was treated with a solution of HCl in ether (2M, 10 mL) at 0° C. The solution stirred at room temperature for 3 hr and was evaporated under reduced pressure. The crude product was triturated with ether, then lyophilised to give the title compound (82 mg, 98%) hplc rt 1.86 min LC-MS MH+ 499; 1H NMR (400 MHZ, DMSO-$d_6$) δ 14.79 (br.s, 1H), 9.00 (s, 1H), 8.21 (br. s, 3H), 8.18 (s, 1H), 7.95 (d, 2H), 7.51 (t, 1H), 7.42 (d, 1H), 3.97 (t, 2H), 3.63 (s, 3H), 3.43 (t, 2H), 3.19 (t, 2H), 2.98 (s, 3H), 2.81 (s, 3H), 2.68 (t, 2H), 2.08 (s, 3H).

Example 4

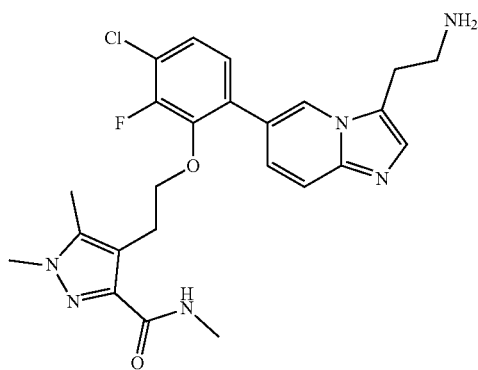 [SMILES: CNC(=O)c1nn(C)c(C)c1CCOc1c(-c2ccc3ncc(CCN)n3c2)ccc(Cl)c1F]

4-(2-{6-[3-(2-aminoethyl)imidazo[1,2-a]pyridin-6-yl]-3-chloro-2-fluorophenoxy}ethyl)-N,1,5-trimethyl-1H-pyrazole-3-carboxamide Step 1

A solution of 4-(2-{6-[3-(2-{[(tert-butoxy)carbonyl]amino}ethyl)imidazo[1,2-a]pyridin-6-yl]-3-chloro-2-fluorophenoxy}ethyl)-1,5-dimethyl-1H-pyrazole-3-carboxylic acid (Intermediate 2, 250 mg, 0.44 mmol) in THF (2 mL) was added methylamine (2M, in THF, 0.65 mL, 1.31 mmol) followed by triethylamine (0.31 mL, 2.18 mmol), EDC hydrochloride (126 mg, 0.66 mmol) and hydroxybenztriazole (89 mg, 0.66 mmol) and the reaction mixture was stirred at rt for 2 days. The reaction mixture was quenched by addition of saturated sodium bicarbonate solution, extracted with ethyl acetate. The organic extract was washed with water, brine, dried over sodium sulphate and concentrated. The crude product was purified by prep TLC (3% MeOH/DCM), followed by preparative hplc to give tert-butyl N-{2-[6-(4-chloro-2-{2-[1,5-dimethyl-3-(methylcarbamoyl)-1H-pyrazol-4-yl]ethoxy}-3-fluorophenyl)imidazo[1,2-a]pyridin-3-yl]ethyl}carbamate (100 mg, 39%). 1H NMR (400 MHZ, DMSO-$d_6$) δ 7.75 (d, 1H), 7.52 (d, 1H), 7.44 (s, 1H), 7.40 (t, 1H), 7.36 (d, 1H), 7.28 (d, 1H), 6.98 (dd, 1H), 4.03 (t, 2H), 3.62 (s, 3H), 3.28 (t, 2H), 3.03 (t, 2H), 2.89 (t, 3H), 2.63 (d, 3H), 1.91 (s, 3H), 1.30 (d, 9H).

Step 2

According to the general method for Boc deprotection (method A) tert-butyl N-{2-[6-(4-chloro-2-{2-[1,5-dimethyl-3-(methylcarbamoyl)-1H-pyrazol-4-yl]ethoxy}-3-fluorophenyl)imidazo[1,2-a]pyridin-3-yl]ethyl}carbamate (100 mg, 0.17 mmol) was dissolved in ether (2 mL) and was treated with a solution of HCl in ether (2M, 10 mL) at 0° C. The solution stirred at room temperature for 3 hr and was evaporated under reduced pressure. The crude product was triturated with ether, then lyophilised to give the title compound (82 mg, 99%) hplc rt 1.83 min LC-MS MH+ 485; 1H NMR (400 MHZ, DMSO-$d_6$) δ 14.75 (br.s, 1H), 9.00 (s, 1H), 8.17 (br. s, 3H), 8.17 (s, 1H), 7.99 (d, 2H), 7.66 (m, 1H), 7.51 (t, 1H), 7.41 (d, 1H), 4.01 (t, 2H), 3.70 (s, 3H), 3.40 (t, 2H), 3.19 (t, 2H), 2.87 (t, 3H), 2.57 (d, 3H), 2.08 (s, 3H).

Biological Testing

Example (a): HsNMT1 $IC_{50}$

The $IC_{50}$ values for human NMT1 (HsNMT1) of four Example compounds of the invention described above (Examples 1-4) and six comparative examples (Comparative Examples 1, 2, 3, 4, 5 and 6) were measured using a sensitive fluorescence-based assay based on detection of CoA by 7-diethylamino-3-(4-maleimido-phenyl)-4-methylcoumarin, as described in Goncalves, V., et al., Analytical Biochemistry, 2012, 421, 342-344 and Goncalves, V., et al., J. Med. Chem, 2012, 55, 3578.

The structure of the comparative examples are shown below: Comparative Example 1 is Example 70 from WO 2017/001812 (4-(2-{2-[3-(2-aminoethyl)imidazo[1,2-a]pyridin-6-yl]-5-fluorophenoxy}ethyl)-N,N,1,5-tetramethyl-1H-pyrazole-3-carboxamide); Comparative Example 2 is Example 94 from WO 2017/001812 (4-(2-{2-[3-(2-aminoethyl)imidazo[1,2-a]pyridin-6-yl]-5-fluorophenoxy}ethyl)-N,1,5-trimethyl-1H-pyrazole-3-carboxamide); Comparative Example 3 is Example 71 from WO 2017/001812 ([2-(6-{4-fluoro-2-[2-(1,3,5-trimethyl-1H-pyrazol-4-yl)ethoxy]phenyl}imidazo[1,2-a]pyridin-3-yl)ethyl](methyl)amine); Comparative Example 4 is Example 78 from WO 2017/001812 (4-[2-(2-{3-[(dimethylamino)methyl] imidazo[1,2-a]pyridin-6-yl}-5-fluorophenoxy)ethyl]-N,N,1,5-tetramethyl-1H-pyrazole-3-carboxamide); Comparative Example 5 is Example 17 from WO 2017/001812 (1-(5-(4-fluoro-2-(2-(1,3,5-trimethyl-1H-pyrazol-4-yl)ethoxy)phenyl)-1-methyl-1H-indazol-3-yl)-N,N-dimethylmethanamine); and Comparative Example 6 is Example 30 from WO 2017/001812 (1-(5-(3-fluoro-2-(2-(1,3,5-trimethyl-1H-pyrazol-4-yl)ethoxy)phenyl)-1-methyl-1H-indazol-3-yl)-N,N-dimethylmethanamine). Methods for synthesizing Comparative Example 1, 2, 3, 4, 5 and 6 are provided in WO 2017/001812.

Comparative Example 1

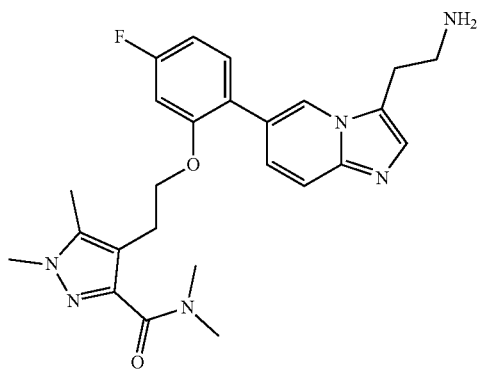

(Example 70 from WO 2017/001812)

Comparative Example 2

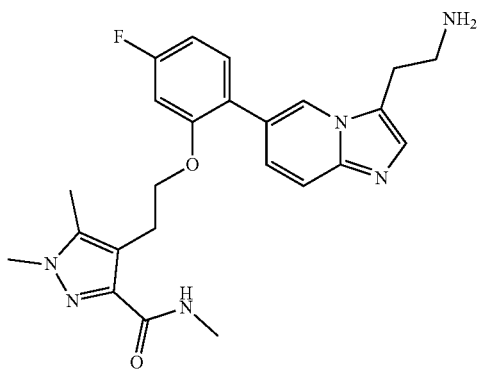

(Example 94 from WO 2017/001812)

Comparative Example 3

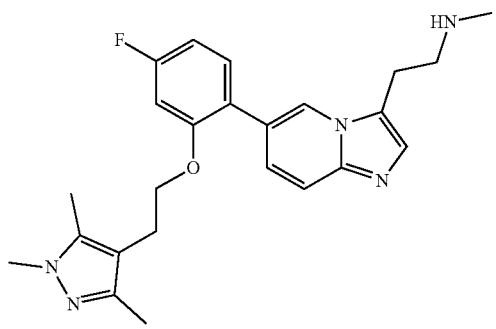

(Example 71 from WO 2017/001812)

Comparative Example 4

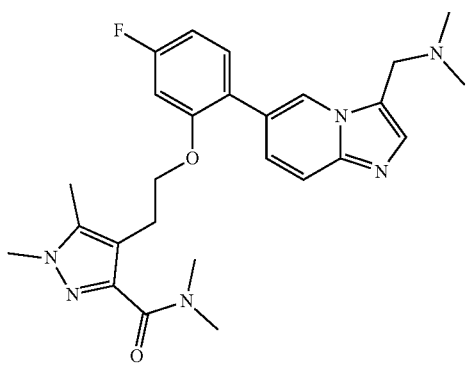

(Example 78 from WO 2017/001812)

Comparative Example 5

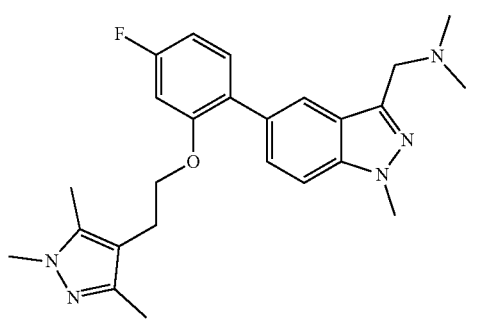

(Example 17 from WO 2017/001812)

Comparative Example 6

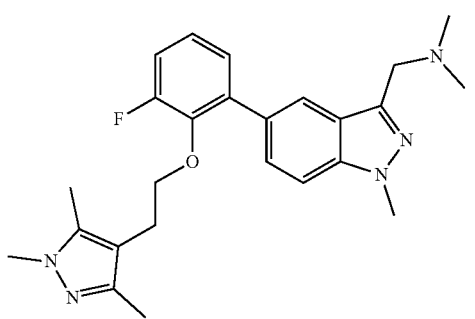

(Example 30 from WO 2017/001812)

Comparative Examples 1 and 2 are most structurally similar to the compounds of the invention. Comparative Examples 5 and 6 are most structurally similar to the known potent human NMT inhibitor IMP-1088 (which is disclosed in WO2017/001812 (Imperial Innovations Limited) as compound 49).

Results

HsNMT1 $IC_{50}$ values for Example compounds 1~4 of the invention are provided in the Table 3, below. Table 3 also shows HsNMT1 $IC_{50}$ values for Comparative Examples 1, 2, 3, 4, 5 and 6.

The Example compounds and Comparative Examples 1, 2 and 4 all had HsNMT1 $IC_{50}$ values of around 1 nM, which is the lowest measureable threshold of this assay (i.e. the compounds are potent beyond the measureable sensitivity of the enzyme inhibition assay). As such, to distinguish the potency of these compounds multiple cell line assays (a metabolic activity assay and a CellTiter-Blue @ Assay) were used to distinguish the potency of the compounds, as described below.

Example (b) Metabolic Activity Assay (MTS Assay)

Example NMT inhibitors of the present invention were tested for activity in an in vitro metabolic activity assay using the human cell line MRC5. Comparative Examples 1, 2, 3, 4, 5 and 6 were also tested in the same metabolic activity assay. Compounds having activity in inhibiting metabolic activity in the assay are expected to be useful as agents for preventing and/or treating cancer, by virtue of being inhibitors of human NMT1 and/or NMT2. The compounds with the highest activity in the assay are expected to be the most potent inhibitors of human NMT1 and/or NMT2.

Cell Preparation:

MRC5 cells (obtained from Dr David Mann's group, Imperial College; cell type: fibroblasts cells which derive from normal lung tissue) were grown in DMEM media (supplemented with 10% FBS) and were seeded in a 96-well plate, 24 h prior to treatment. Cell suspensions were prepared by adjusting the cell density to the appropriate concentration (as stated in the Table 1 below) and 50 µL of the cell suspension was transferred to wells B-G in columns 2-11 of a 96-well plate.

TABLE 1

| Number of cells plated | |
| --- | --- |
| | MRC5 |
| Cell suspension concentration (cells/mL) | 38,000 |
| cells per well | 1,900 |

Assay Procedure:

100 µL of growth media (DMEM media) containing 0.2% DMSO was added to wells B-G in columns 2 and 11 as positive controls, and 100 µl of growth media containing Puromycin (3 µg/mL; final concentration in the plate 2 µg/mL) was added to wells B-G in column 3 as a negative control. Seven concentrations of NMT inhibitor stock solution were prepared for each Example (Example 1 and 2) and each Comparative Example (Comparative Examples 1, 2, 3, 4, 5 and 6) tested (same final percentage of DMSO, dilution factor=3 starting from 15 µM or 150 µM). 100 µL of inhibitor stock solution was added to wells B-G in columns 4-10 of a 96-well plate (final concentration of Example compound or Comparative Example compound in the plate starting from 10 µM or 100 µM; total volume in each well was 150 µL). The plate was incubated at 37° C. with 5% $CO_2$ level.

After 72 h, 20 µL MTS reagent (Promega, prepared according to the supplier protocol) was added to each well of the 96-well plate. The plate was incubated at 37° C. for 2 h and the absorbance per well was measured at 490 nm with an EnVision plate reader. The average absorbance value of the negative control (Puromycin-treated cells) was subtracted from each value and the metabolic activity was calculated as a percentage relative to the positive control (DMSO-treated cells). $EC_{50}$ values were calculated using GraphPad.

Results $EC_{50}$ values for Example compounds 1 and 2 for the MRC5 cell line are provided in Table 3, below. Table 3 also shows $EC_{50}$ values for Comparative Examples 1, 2, 3, 4, 5 and 6 for the MRC5 cell line.

As can be seen from these results, Example compounds 1 and 2 showed the highest activity in the metabolic activity assay, having $EC_{50}$ values of less than 40 nM in the MRC5 cell line, thus indicating that these compounds are very potent inhibitors of human NMT, and are useful as anticancer agents. Comparative Example 6 also showed high activity in the metabolic activity, and Comparative Example 4 had relatively high activity in the metabolic activity. Comparative Examples 1, 2, 3 and 5 were significantly less active in the metabolic activity cell line assay.

Example (c) CellTiter-Blue® Assay

Example NMT inhibitors of the present invention were tested for activity in in vitro CellTiter-Blue® assays using the human cell line MDA MB 231, LY 12318, or BL-41. Comparative Examples 1 and 2 were also tested in the same assays. Compounds having activity in inhibiting metabolic activity in the assay are expected to be useful as agents for preventing and/or treating cancer, by virtue of being inhibitors of human NMT1 and/or NMT2. The compounds with the highest activity in the assay are the most potent inhibitors of human NMT1 and/or NMT2.

MDA MB 231 cells (obtained from Professor Eric Aboagye, Hammersmith Hospital; cell type: triple negative breast cancer) were grown in low glucose DMEM in 5% $CO_2$ media (supplemented with 10% FBS); LY 12318 cells (obtained from Dr Martin Janz, Max Delbrueck Center; cell type: B cell lymphoma patient derived xenograft) were grown in DMEM media (supplemented with 10% FBS); and BL-41 cells (obtained from Cell Services at the Crick Institute; cell type: Burkitt's Lymphoma) were grown in RPMI-1640 media in 5% $CO_2$ (supplemented with 10% FBS). The MDA MB 231 cells, LY 12318 cells or BL-41 cells were seeded in 96-well plates, 24 h prior to treatment. Cell suspensions were prepared by adjusting the cell density to the appropriate concentration (as stated in the Table 2 below) and 50 µL of the cell suspension was transferred to wells B-G in columns 2-11 of a 96-well plate.

TABLE 2

| Number of cells plated | | | |
| --- | --- | --- | --- |
| | MDA MB 231 | LY 12318 | BL-41 |
| Cell suspension concentration (cells/mL) | 70,000 | 500,000 | 500,000 |
| cells per well | 3,500 | 25,000 | 35,000 |

Twenty-four hours later, 50 µl of growth media (low glucose DMEM in 5% $CO_2$ media supplemented with 10% FBS for MDA MB 231 cells; DMEM media in 5% $CO_2$ supplemented with 10% FBS for LY 12318 cells; or RPMI-1640 media supplemented with 10% FBS for BL-41 cells) containing 0.0004% DMSO (positive control), a mix of Puromycin and Staurosporine (negative controls, final concentration 2 µg/mL and 1 µM respectively) or different concentrations of each Example (Example 1 and 2) or each Comparative Example (Comparative Example 1 and 2) (dilution factor=3, starting at 2 µM, final concentration in the plate starting from 10 µM) were prepared and added to a well of the 96-well plate. The plate was incubated at 37° C. with 5% $CO_2$ level.

72 hours later, 20 µl/well CellTiter-Blue® (G8081, Promega) were added to the plates according to the manufacturer's protocol, the plate was incubated at 37° C. for 4 h for MDA MB 231 cells and BL-41 cells, or 3 h for LY 12318 cells, followed by measuring the absorbance per well at 570 nm using an EnVision plate reader. The negative control values were subtracted from every value. The metabolic activity was calculated as a percentage relative to the positive control. The $EC_{50}$ values were calculated using GraphPad Prism.

Results $EC_{50}$ values for Example compounds 1 and 2 in the MDA MB 231, LY 12318 and BL-41 cell lines are provided in the Table 3, below. Table 3 also shows $EC_{50}$ values for Comparative Examples 1 and 2 for the MDA MB 231, LY 12318 and BL-41 cell lines.

Figure 2:
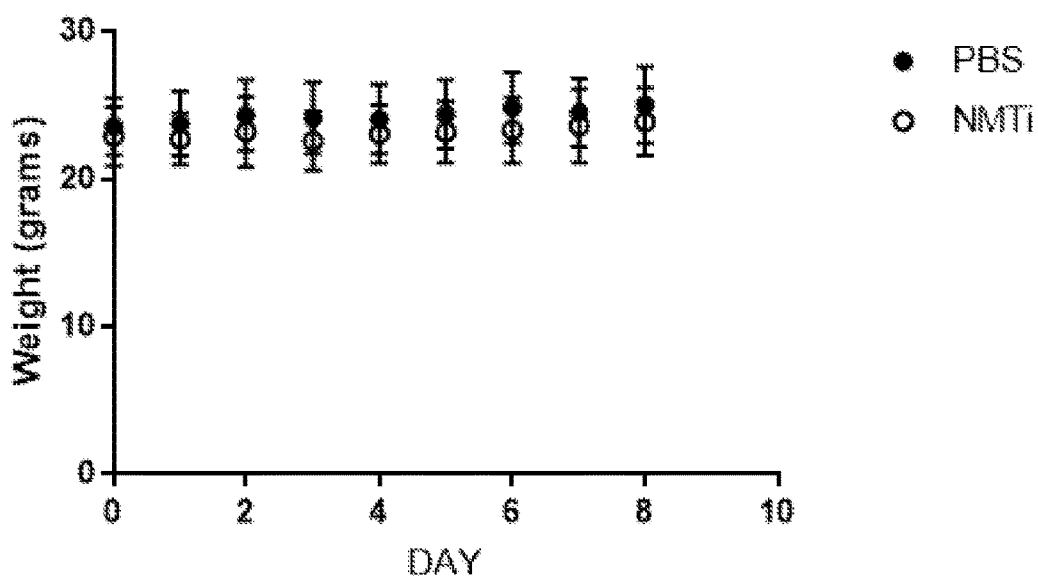
FIG. 2 shows the average weight of mice injected with MDA MB 231 cells and having a tumour of at least 50 mm3 mass treated with Example 1 ("NMTi") or control (phosphate buffered saline ("PBS")) over a 10 day period.

As can be seen from these results, Example compounds 1 and 2 showed the highest activity in the CellTiter-Blue® assays, having $EC_{50}$ values of less than 70 nM in each cell line, indicating that the compounds are useful as anti-cancer agents. Comparative Examples 1 and 2 were significantly less active in each cell line tested. Example compounds 3 and 4 were potent inhibitors of HsNMT1 although they appeared to be less potent than Example compounds 1 and 2.

experiments were carried out under London Home Office license authority and London Home Office Ethics Committee guidelines. When the tumour mass reached 50 mm3, the animals were randomized (8 per group) and treated for 10 days with PBS solution (control group) or 25 mg/kg of Example 1 suspended in PBS twice a day by oral gavage. Tumor growth rates were analyzed by caliper measurements every day after the start of the treatment period with Example 1 ("NMTi") or the control ("PBS"). Tumor volume was calculated according to the formula: (length×width)/2. Weight of the mice was also measured every day after the start of the treatment period with Example 1 ("NMTi") or the control ("PBS"). Mice were euthanised when the tumor size exceeded 15 mm in diameter in any direction. FIG. 1 shows the average tumor growth rates, and FIG. 2 shows the weight, for mice over the 10 day treatment period with Example 1 ("NMTi") or the control ("PBS").

TABLE 3

Results of Examples (a), (b) and (c)

| Compound* | HsNMT1 $IC_{50}$ (nM) | MRC5 $EC_{50}$ (nM) | MDA-MB-231 $EC_{50}$ (nM) | LY12318 $EC_{50}$ (nM) | BL-41 $EC_{50}$ (nM) |
|---|---|---|---|---|---|
| Example Compound 1 | 1.5 | 13 | 20 | 27 | 14 |
| Example Compound 2 | 0.4 | 37 | 45 | 69 | 24 |
| Example Compound 3 | 4.2 | | | | |
| Example Compound 4 | 6.3 | | | | |
| Comparative Example 1 (Example 70 from WO2017001812) | 2 | 450 | 285 | 246 | 91 |
| Comparative Example 2 (Example 94 from WO2017001812) | 1 | >6800 | 237 | >370 | 298 |
| Comparative Example 3 (Example 71 from WO2017001812) | 10.5 | 5400 | | | |
| Comparative Example 4 (Example 78 from WO2017001812) | 1 | 63 | | | |
| Comparative Example 5 (Example 17 from WO2017001812) | 13 | 27000 | | | |
| Comparative Example 6 (Example 30 from WO2017001812) | 5 | 38 | | | |

*the results were gathered in more than one experiment and in particular the results for Examples 3 and 4 were gathered at a later time than the results on Examples 1 and 2

Example (d) In Vivo Study in Mice

The effect of Example 1 on tumor growth rate in mice was also investigated.

$5 \times 10^6$ MDA MB 231 cells (obtained from Professor Eric Aboagye, Hammersmith Hospital; cell type: triple negative breast cancer) were resuspended in PBS, and 50 µl of cells/PBS was mixed with 50 µl of Matrigel to provide a total volume of 100 µL containing 50% Matrigel. The suspension was injected into the right flank in 16 Athymic Nude female mice. Mice were five to six weeks old and obtained from Charles Rivers Laboratories. All of the

Results

As can be seen from FIG. 1, the tumour growth rate was reduced in mice treated with Example 1 of the present invention, showing that compounds of the invention have or are expected to have anti-tumour activity in vivo. Further, the data also demonstrates that compounds of the invention are or are expected to be effective when administered orally, and thus are orally bioavailable. No weight change in the mice was observed.

Metabolic stability of the compounds of the invention was also investigated:

Example (e): Rat Hepatocyte Half Life

Example Compound 1 was tested for metabolic stability in rat metabolic assays using hepatocytes derived from pooled male Sprague-Dawley rats. Comparative Examples 2, 3 and 4 were also tested in the same assay. Compounds having good metabolic stability in the assay are expected to be especially useful as agents for preventing and/or treating cancer, by having a long half-life in human patients.

Frozen pooled rat hepatocytes obtained from LifeTechnologies were thawed and purified according to the manufacturer's instructions. The test compound (4 mM) in DMSO was diluted with acetonitrile to provide a 100 µM sub-stock then further diluted with pH7.4 Krebs-Henseleit buffer supplemented with $CaCl_2$), $NaHCO_3$, HEPES, fructose and glycine) to provide a 2 µM working solution. 25 µL of working solution was incubated at 37° C., treated with 25 µL of rat hepatocyte suspension (containing $1 \times 10^6$ cells/mL) and incubated at 37° C. with 5% $CO_2$ level at 95% relative humidity. Wells were incubated for an appropriate time (0, 15, 30, 45, 60 and 75 min) then quenched with 250 µL of acetonitrile containing reference standards diltiazem, 7-ethoxycoumarin and propranolol). The plates were shaken, sonicated for 5 min then cooled to 4° C. until all sampling was complete. All plates were centrifuged at 4000 rpm for 20 min to pellet the debris. 110 µl supernatant was diluted 110 µL water and quantitated using LC-MS/MS.

The results were used to calculate the % Remaining of the test compound at time point t=100×~[(AUC at time point t)/(AUC at T=0)]. A linear regression curve was fitted to a plot of natural logarithm (ln) of AUC against time. The T-half (min)=0.693/slope

Results

Rat hepatocyte half-life times for Example Compound 1 and for Comparative Examples 2, 3 and 4 are provided in Table 4. These results show that Example Compound 1 has good metabolic stability in vitro. As such, it is expected that the compounds of the invention will be especially useful as medicaments, and in particular for use as medicaments for preventing and/or treating cancer by having a long half-life in human patients. Comparative Examples 3 and 4 had had significantly shorter half-lives.

Example (f): Rat or Mouse Half Life

Example Compound 1, and Comparative Examples 2 and 3 were tested for metabolic stability in male Sprague-Dawley rats. Comparative Example 5 was tested for metabolic stability in male CD-1 mice. Compounds having good metabolic stability in rats or mice are expected to be especially useful as agents for preventing and/or treating cancer, by having a long half-life in human patients.
Rat Protocol:
Male Sprague-Dawley rats were fasted for 4 h before dosing. Groups of 3 rats were dosed with Example Compound 1, Comparative Example 2, or Comparative Example 3
  (i) intravenously at a dose of 1 mg/kg using a dose volume 2 mL/kg where the animals are anaesthetized using 3% v/v isoflurane:oxygen mixture and dose administered through lateral tail vein; or
  (ii) orally by gavage (OG) at a dose of 3 mg/kg using a dose volume 5 ml/kg to conscious animals.

~100 µL blood sample were collected after 5 min, 15 min, 30 min, 1 h, 2 h, 4 h, 8 h and 24 h (intravenous) and 15 min, 30 min, 1 h, 2 h, 4 h, 8 h and 24 h (oral) and transferred to heparinized capillary tubes, and subsequently into 0.5 mL microcentrifuge tubes. All blood samples are processed for plasma by centrifugation at 1640×g for 5 min at 4° C. within half an hour of collection. Plasma samples were stored at −20° C. until all samples were collected. All samples were mixed with ice-cold acetonitrile containing an internal standard (IS) in 1:4 v/v and centrifuged at 4000 rpm for 15 min at 15° C. Supernatant was then half diluted in water and loaded for LCMS/MS analysis. Analyte peak area/IS peak area (the ratio) was considered for further data analysis as described below.

Calibration curve and QC samples: Compound stock was prepared and further serial dilutions were carried out. The samples were spiked in blank plasma (1:50). Calibration curve ranged from 1 to 1250 ppb. Three quality control samples were also prepared-high QC (HQC), Mid QC (MQC and Low QC (LQC).
Mouse Protocol:
Same as rat protocol except that CD-1 mice were dosed at 5 mg/kg iv and 10 mg/kg po.

Results

Rat oral half-life times for Example Compound 1 and Comparative Examples 2 and 3 are provided in Table 4. Mouse oral half-life time for Comparative Example 5 is also provided in Table 4. These results show that Example Compound 1 has good metabolic stability in vivo. As such, it is expected that the compounds of the invention will be especially useful as medicaments, and in particular for use as medicaments for preventing and/or treating cancer by having a long half-life in human patients. Comparative Examples 3 and 5 had significantly shorter in vivo half lives compared to Example Compound 1.

Example (g): Human Liver Microsomes Half Life

Example Compound 1 was tested for metabolic stability in an assay using human liver microsomes. Comparative Examples 2, 3, 4, 5 and 6 were also tested in the same assay. Compounds having good metabolic stability in the assay are expected to be especially useful as agents for preventing and/or treating cancer, by having a long half-life in human patients Frozen human liver microsomes obtained from Corning, USA (cat #452117) were thawed and diluted with 100 mM of pH 7.4 phosphate buffer to give a 1 mg/ml solution. An NADPH regeneration system (NRS) was prepared as a solution containing 13 mM NADP, 33 mM glucose-6-phosphate, 33 mM $MgCl_2$ and 4U/mL glucose-6-phosphate dehydrogenase in 100 mM of pH7.4 phosphate buffer. The test compound (4 mM) in DMSO was diluted with acetonitrile to provide a 100 µM sub-stock then further diluted with 100 mM of pH7.4 phosphate buffer to provide a 2 µM working solution. The liver microsome solution and NRS were incubated at 37° C. before use. To each well of the test plate was dispensed 60 µL of buffer, 50 µL of test compound solution and 10 µL of NRS. A reaction was initiated by addition of 40 µL of liver microsome solution. Wells were incubated for an appropriate time (0, 5, 10, 20, 30 and 60 min) then quenched with 300 µL of acetonitrile containing reference standards atenolol, propranolol, diclofenac, verapamil). All plates were centrifuged at 3500 rpm for 20 min at 15° C. to pellet the debris. 110 µL supernatant was diluted 110 µL water and quantitated using LC-MS/MS.

The results were used to calculate the % Remaining of the test compound at time point t=100×~[(AUC at time point t)/(AUC at T=0)]. A linear regression curve was fitted to a plot of natural logarithm (ln) of AUC against time. The T-half (min)=0.693/slope.

Results

The half-life times for Example Compound 1 and Comparative Examples 2, 3, 4, 5 and 6 in human liver microsomes are provided in Table 4. These results show that Example Compound 1 has good metabolic stability in vitro. As such, it is expected that the compounds of the invention will be especially useful as medicaments, and in particular for use as medicaments for preventing and/or treating cancer by having a long half-life in human patients. Comparative Examples 3 to 6 all have significantly shorter half-lives compared to Example Compound 1.

TABLE 4

| Compound | Rat Hepatocyte t ½ (min) | Rat or mouse t ½ (h) | Human liver microsomes t ½ (min) |
| --- | --- | --- | --- |
| Example Compound 1 | 80 | 7.1 (rat) | 67 |
| Comparative Example 2 (Example 94 from WO2017001812) | 81 | 8.3 (rat) | 117 |
| Comparative Example 3 (Example 71 from WO2017001812) | 46 | 4.5 (rat) | 37 |
| Comparative Example 4 (Example 78 from WO2017001812) | 32 | | 12 |
| Comparative Example 5 (Example 17 from WO2017001812) | | 0.7 (mouse) | 7 |
| Comparative Example 6 (Example 30 from WO2017001812) | | | 4 |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A compound which is: 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide:

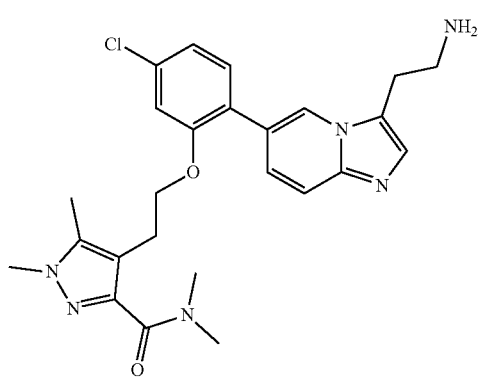 [SMILES: Cc1c(CCOc2cc(Cl)ccc2-c2ccc3ncc(CCN)n3c2)c(C(=O)N(C)C)nn1C]

or
4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide:

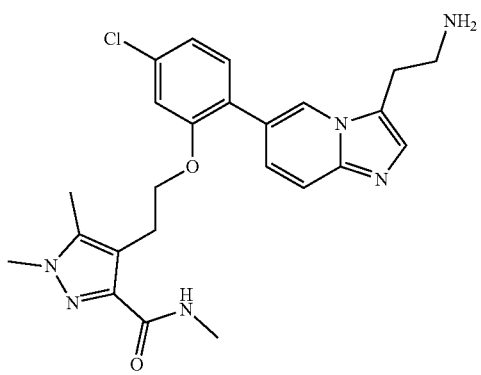

or a pharmaceutically acceptable amide, carbamate or salt of any one thereof, including a salt of said amide or carbamate.

2. The compound as claimed in claim 1, wherein the compound is 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide:

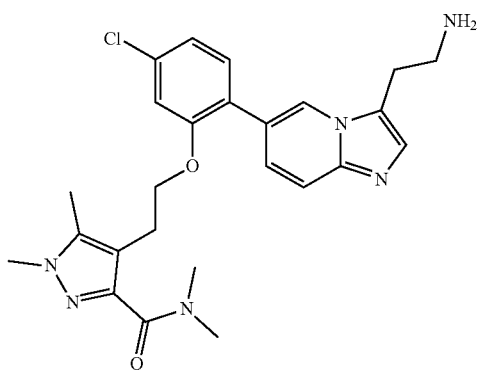 [SMILES: Cc1c(CCOc2cc(Cl)ccc2-c2ccc3ncc(CCN)n3c2)c(C(=O)N(C)C)nn1C]

or a pharmaceutically acceptable amide, carbamate or salt thereof, including a salt of said amide or carbamate.

3. A pharmaceutical composition comprising a compound as claimed in claim 1, together with a pharmaceutically suitable carrier.

4. The composition as claimed in claim 3, which also contains a further therapeutic agent.

5. A method of treating lymphoma or breast cancer in which inhibition of N-myristoyl transferase provides a therapeutic effect in a subject, comprising administering a therapeutically effective amount of a compound as claimed in claim 1 to the subject.

6. A kit of parts comprising: (a) a first pharmaceutical composition comprising a compound as claimed in claim 1 and a pharmaceutically acceptable carrier; and (b) a second pharmaceutical composition comprising a further therapeutic agent.

7. The compound as claimed in claim 1, wherein the compound is 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide:

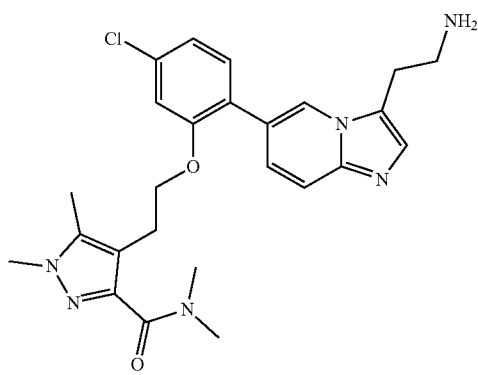

or a pharmaceutically acceptable salt thereof.

8. A method of treating lymphoma or breast cancer in which inhibition of N-myristoyl transferase provides a therapeutic effect in a subject, comprising administering a therapeutically effective amount of a compound as claimed in claim 7 to the subject.

9. A pharmaceutical composition comprising a compound as claimed in claim 7, together with a pharmaceutically suitable carrier.

10. The compound according to claim 1, which is 4-(2-{2-[3-(2-aminoethyl)imidazo[1,2-a]pyridin-6-yl]-5-chlorophenoxy}ethyl)-N,1,5-trimethyl-1H-pyrazole-3-carboxamide):

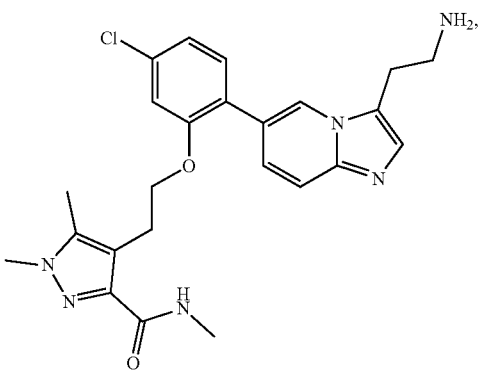 [SMILES: CNC(=O)c1nn(C)c(C)c1CCOc1cc(Cl)ccc1-c1ccc2ncc(CCN)n2c1]

or a pharmaceutically acceptable amide, carbamate or salt thereof, including a salt of said amide or carbamate.

* * * * *